United States Patent [19]
Thornander et al.

[11] Patent Number: 4,712,555
[45] Date of Patent: Dec. 15, 1987

[54] PHYSIOLOGICALLY RESPONSIVE PACEMAKER AND METHOD OF ADJUSTING THE PACING INTERVAL THEREOF

[75] Inventors: Hans T. Thornander, Paris, France; John W. Poore, Chatsworth, Calif.; Jason A. Sholder, Canoga Park, Calif.; James R. Thacker, Saugus, Calif.; David C. Amundson, Pacific Palisades, Calif.

[73] Assignee: Siemens-Elema AB, Solna, Sweden

[21] Appl. No.: 716,831

[22] Filed: Mar. 27, 1985

Related U.S. Application Data

[63] Continuation-in-part of Ser. No. 662,723, Oct. 19, 1984.

[51] Int. Cl.$^4$ .............................................. A61N 1/36
[52] U.S. Cl. ............................................. 128/419 PG
[58] Field of Search .................. 128/419 PG, 419 PT

[56] References Cited

U.S. PATENT DOCUMENTS

| | | | |
|---|---|---|---|
| 3,593,718 | 7/1971 | Krasner | 128/419 |
| 4,009,721 | 4/1976 | Alcidi | 128/419 |
| 4,055,189 | 10/1977 | Auerbach et al. | 128/419 PG |
| 4,140,132 | 3/1978 | Dahl | 128/419 |
| 4,181,133 | 1/1980 | Kolenik et al. | 128/419 PG |
| 4,202,339 | 5/1980 | Wirtzfeld | 128/419 |
| 4,228,803 | 10/1980 | Rickards | 128/419 PG |
| 4,305,396 | 12/1981 | Wittkampf | 128/419 |
| 4,378,020 | 3/1983 | Nappholz et al. | 128/419 PG |
| 4,428,378 | 1/1984 | Anderson | 128/419 |
| 4,436,092 | 3/1984 | Cook | 128/419 |
| 4,467,807 | 8/1984 | Bornzin | 128/419 |
| 4,503,857 | 3/1985 | Boute et al. | 128/419 PG |
| 4,515,161 | 5/1985 | Wittkampf et al. | 128/419 PG |
| 4,527,568 | 7/1985 | Rickards | 128/419 |

OTHER PUBLICATIONS

Krasner et al, A Physiologically Controlled Cardiac Pacemaker, JAAMI, Nov./Dec. 1966, pp. 14–20.
Voukydis et al, A Physiologically Regulated Cardiac Pacemaker, Brit. J. of Experimental Pathology, vol. 48, pp. 118–123, (1967).
Twizell, A Noise-Protected Digital Heart Ratemeter, Radio & Elec. Engr., vol. 45, No. 4, pp. 155–160, Apr. 1975.

*Primary Examiner*—William E. Kamm
*Attorney, Agent, or Firm*—Bryant R. Gold; Robert R. Meads

[57] ABSTRACT

A pacemaker and physiological sensor for use therewith that allows the rate at which the pacemaker delivers electrical stimulation pulses to the heart, or the escape interval during which a natural heart event must occur before an electrical stimulation pulse is delivered, to be adjusted as needed in order to satisfy the body's physiological needs. The sensor measures the depolarization time interval between an atrial stimulation pulse, A, and the responsive atrial or ventricle depolarization, P or R respectively, as an indication of the physiological demands placed on the heart. The time interval between a ventricular stimulation pulse, V, and the responsive ventricular depolarization, R, may also be measured and used as an indication of physiological need, and hence as an alternative criteria for rate control. Atrial depolarization is sensed by detecting a P-wave, and ventricular depolarization is preferably sensed by detecting an R-wave. A method of measuring A-P, A-R, or V-R intervals is used to ascertain if these intervals are increasing or decreasing. If, over several heart cycles or beats, an increase or decrease in these measurements is detected, the pacing interval set by the pacemaker is adjusted in an appropriate direction in order to adjust the heart stimulation rate accordingly.

47 Claims, 32 Drawing Figures

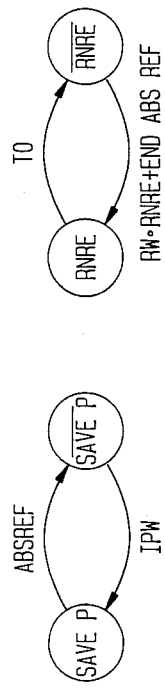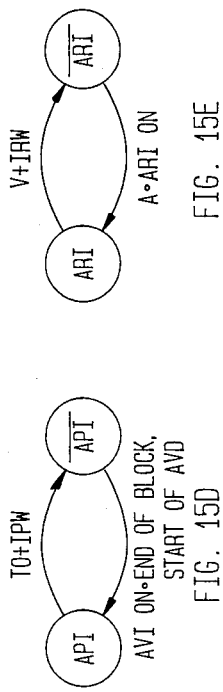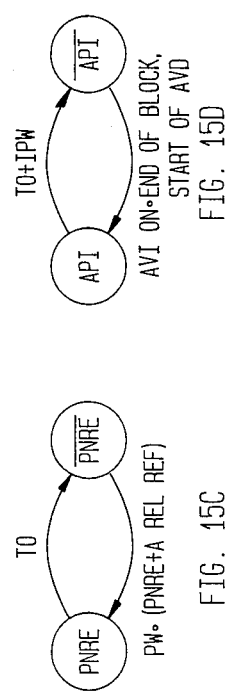
FIG. 15

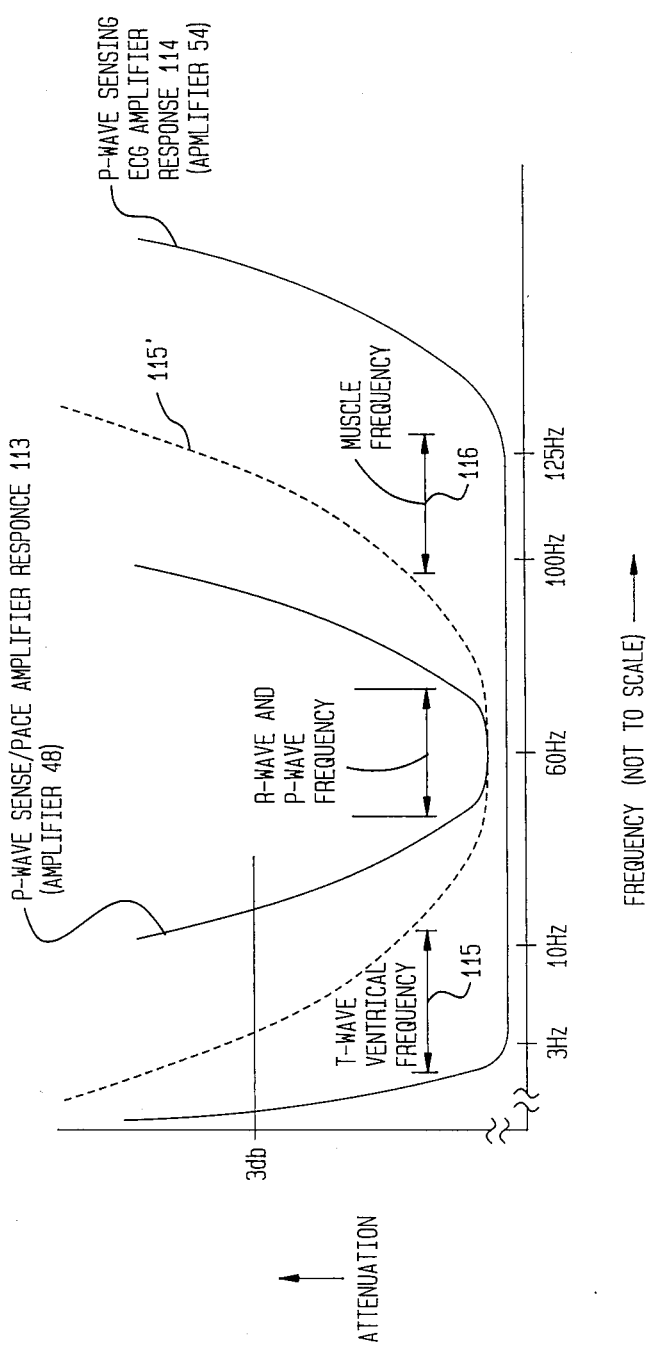

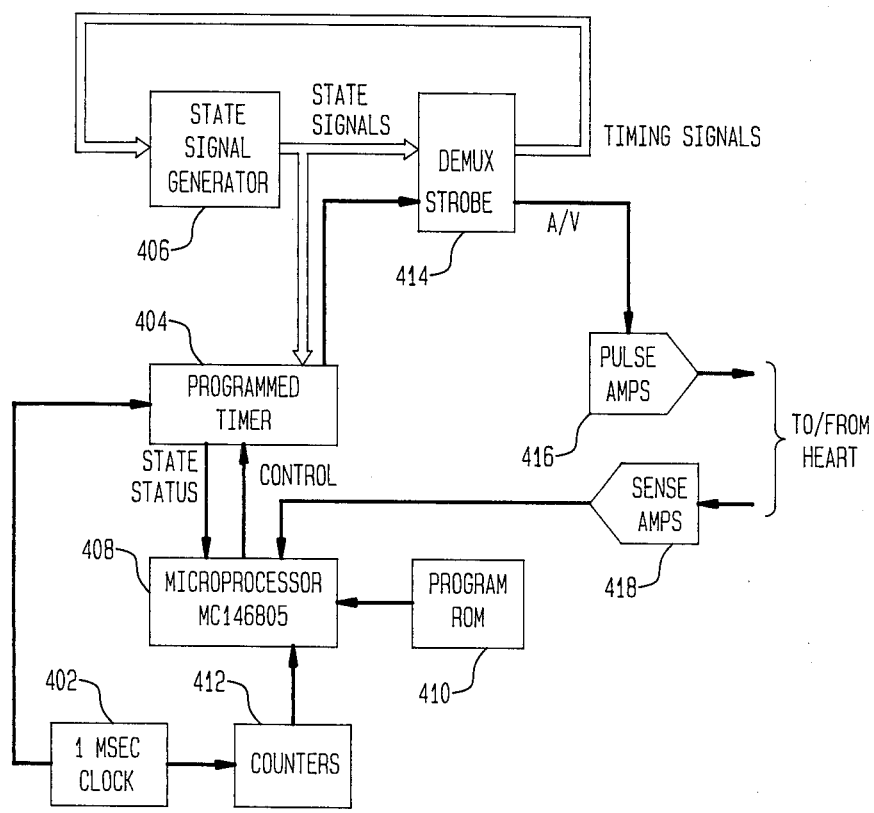
FIG. A-1

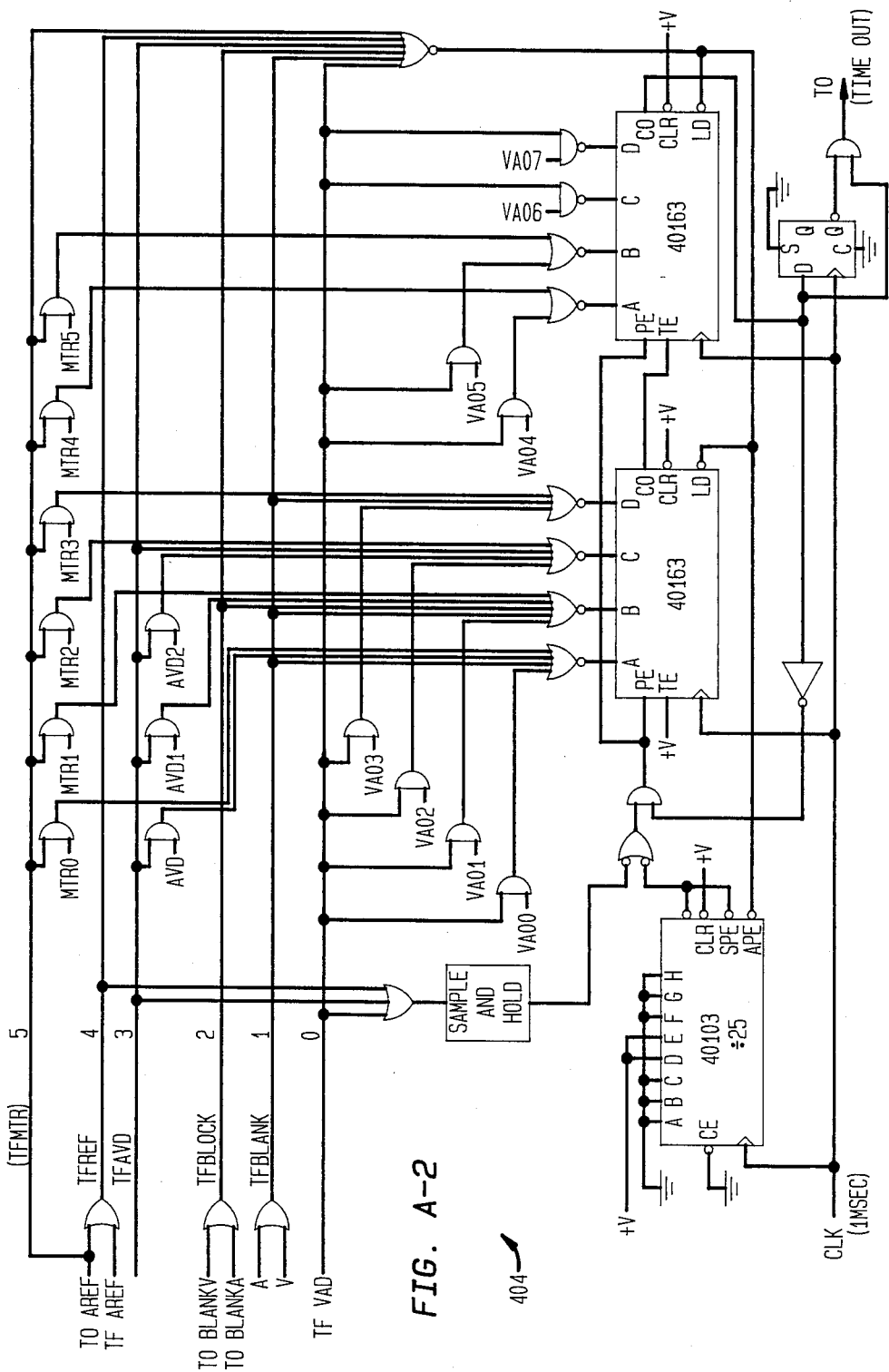
FIG. A-2

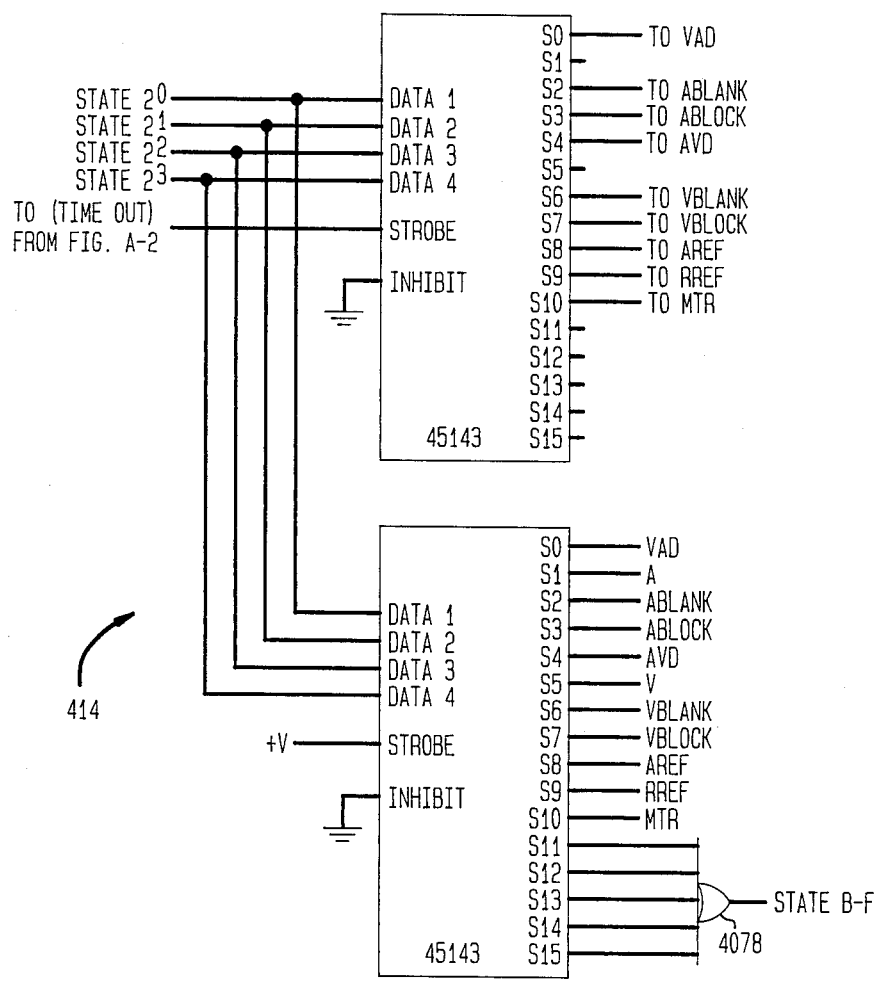
FIG. A-3

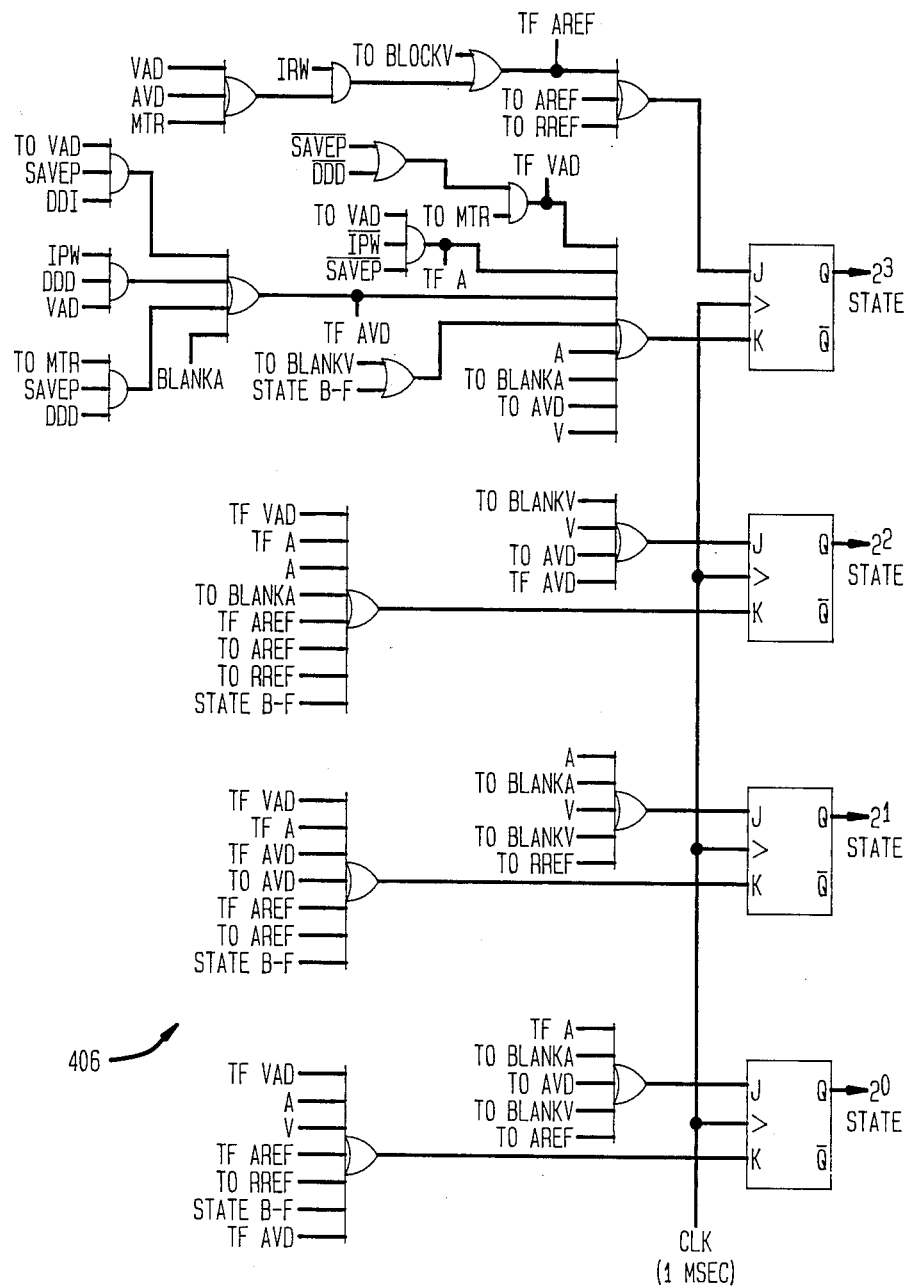
FIG. A-4

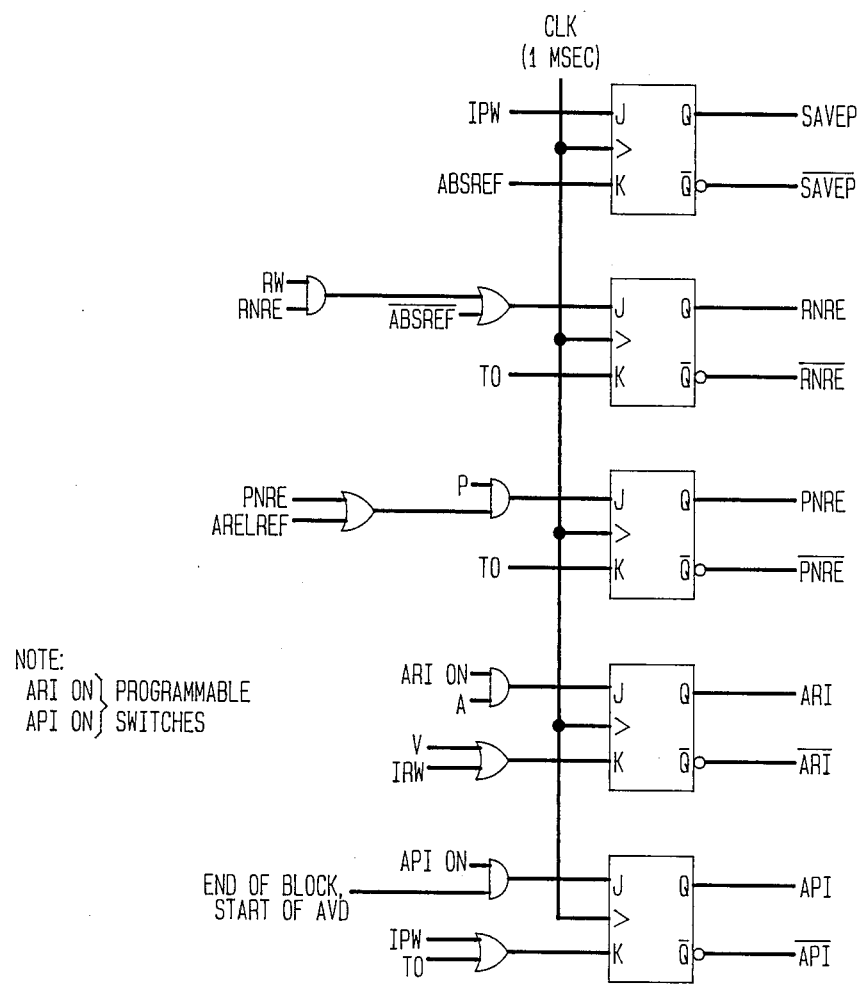
FIG. A-5

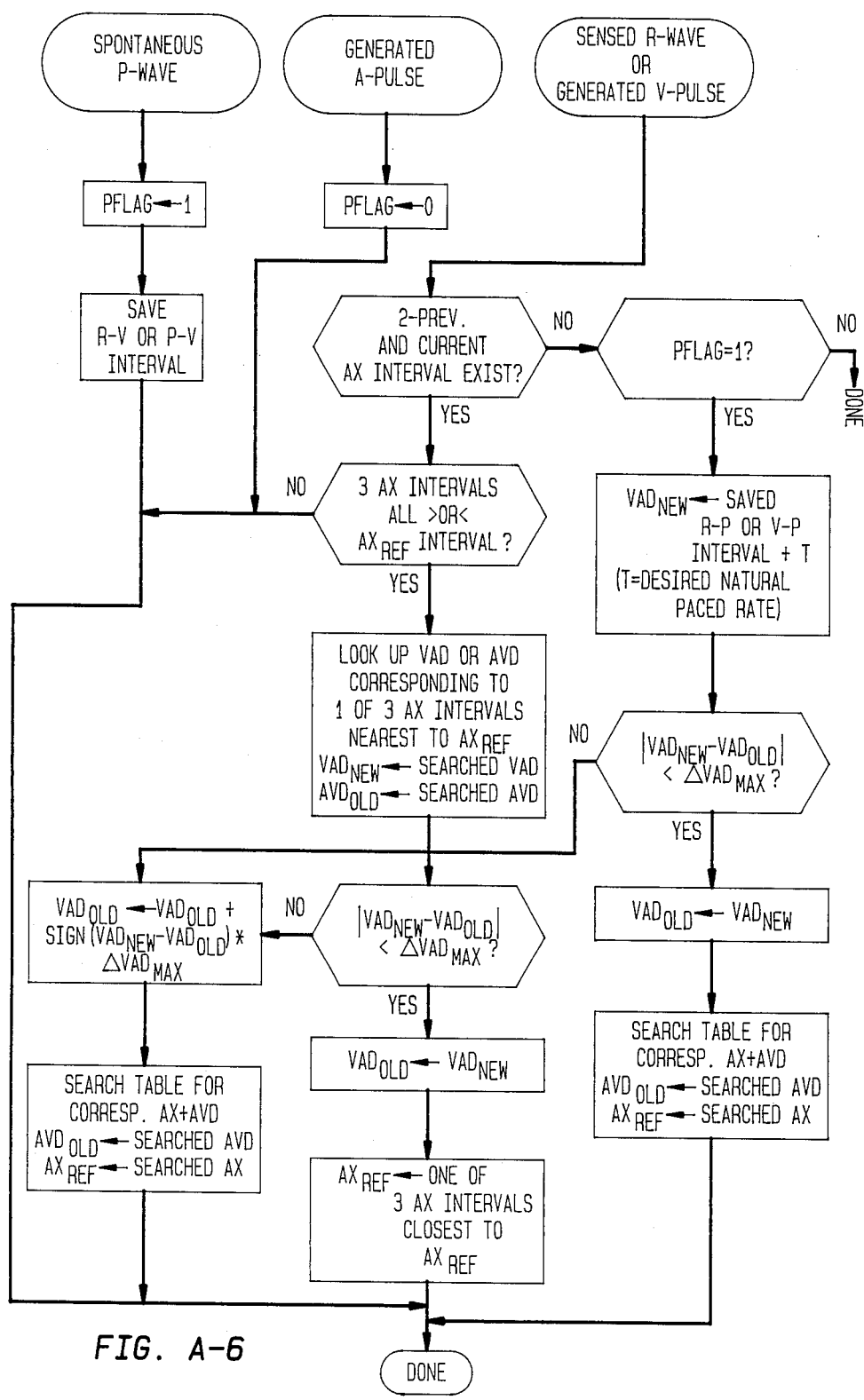
FIG. A-6

PHYSIOLOGICALLY RESPONSIVE PACEMAKER AND METHOD OF ADJUSTING THE PACING INTERVAL THEREOF

CROSS-REFERENCE TO RELATED APPLICATION

This application is a continuation-in-part of application Ser. No. 662,723, filed 10/19/84.

BACKGROUND

The heart is a pump that pumps blood throughout the body. Cardiac pacemakers have long been used to provide stimulation pulses to the heart in order to control the rate at which the heart pumps or beats, thereby controlling the flow rate at which blood is circulated throughout the body. The principal purpose for circulating blood throughout the body, of course, is to deliver oxygen and other nutrients to the body cells, without which oxygen the body cells would soon die. As the body cells are called upon to do more and more work, the flow rate at which oxygenated blood is delivered to the cells must be increased. This increase in flow rate can be achieved by increasing the rate at which the heart beats or pumps. In a normal, healthy, non-paced heart, the heart rate automatically increases in response to the need to deliver more oxygenated blood to the body cells. However, a pacemaker-controlled heart is unable to automatically increase its rate unless the pacemaker is able to sense that an increased oxygen need is present.

Modern pacemakers include complex stimulation pulse generators as well as cardiac event sensors that can pace or sense in the atrium, the ventricle, or both the atrium and ventricle of the heart. Further, such pacemakers include telemetry capabilities so that the activity of the heart and pacemaker can be transmitted to an attending physician or cardiologist. Advantageously, such pacemakers are also programmable so that the same telemetry capabilities can be used by the attending physician or cardiologist in order to adjust the control parameters associated with operation of the pacemaker. Such parameters not only influence the rate at which the pacemaker's stimulation pulses are generated, but also control the pacemaker's basic mode of operation, i.e., the heart chamber that is paced, as well as the heart chamber that is sensed. Hence, modern pacemakers offer great versitility in the manner of their use. Disadvantageously, many modern pacemakers do not yet have the capability to automatically adjust the pacing rate, or pacing interval, in the absence of a sinus P-wave (a sinus P-wave is explained below) as a function of the body's physiological needs unless some sort of physiological sensor external to the pacemaker is employed. As used herein, the term "physiological need" includes the need to change the flow rate at which oxygenated blood is delivered to the body's cells, as well as other body needs that influence the heart rate.

The present invention is directed to an improved pacemaker that includes the capability of automatically adjusting the paced heart rate as a function of sensed physiological needs within the body. Advantageously, no electronic sensors external to the pacemaker need be employed beyond the normal stimulation leads that are connected between the pacemaker and the heart. As is explained more fully below, the present invention senses physiological need by noting changes in a selected time interval associated with the rhythm of the heart.

In the above-referenced earlier-filed application, of which this application is a continuation-in-part, there was disclosed a system and method for determining P-wave capture. Included in the disclosure of the earlier application, much of which is repeated herein, is a reliable method or system for sensing a P-wave that results from an atrial stimulation pulse. As known to those skilled in the art, a P-wave is generated by the atrium of the heart as it depolarizes. Shortly after depolarization, the atrium contracts, which contraction causes the pumping function of the atrium to be realized. While those skilled in the art will recognize that depolarization and contraction are separate events that do not necessarily occur at the same time, the term "contraction" when used hereinafter means depolarization or an event that always occurs in synchrony with depolarization. Because it is extremely helpful for a physician, cardiologist, or other diagnostician to known when the atrium depolarizes and contracts, and whether this depolarization is a result of a pacemaker stimulation pulse or the result of a natural (non-paced) rhythm associated with the heart, reliably sensing a P-wave using signals sensed through the pacemaker leads, especially a P-wave that occurs in response to a stimulation pulse from a pacemaker, has heretofore presented a formidable challenge. Moreover, because the occurance of a P-wave—the occurance of which represents the depolarization of the atrium—is a key cardiac event that helps define a time interval, the measurement of which is associated with at least one embodiment of the present invention, the system and method described in the foregoing earlier-filed application, or equivalents thereof, comprise an important teaching for practicing the invention herein described. Further, because the system and method of P-wave capture described in the earlier application is not limited to sensing P-waves, but can also be used to sense R-waves resulting from a pacing pulse applied to the ventricle, and because the occurrance of an R-wave is likewise a key cardiac event the measurement of which is associated with at least one other embodiment of the invention, the teachings of the earlier-filed application become doubly important.

SUMMARY

It is an object of the present invention to provide a physiological sensor that can sense when the heart rate needs to increase or decrease as a function of the physiological needs of the body within which the heart is located.

It is a further object of the present invention to provide a means for automatically adjusting the pacing rate controlled by a pacemaker as a function of physiological need.

Still a further and related object of the invention is to provide a means for automatically adjusting the escape interval associated with a demand-type pacemaker, which escape interval defines the time interval within which a natural heart event (such as an atrial or ventricular depolarization) must occur in order to inhibit the delivery of a stimulating pulse to the heart, said escape interval being adjusted by the adjustment means of the present invention so as to increase or decrease the rate at which the heart beats in accordance with physiological need.

Yet another object of the invention is to provide a pacemaker that includes means for selectively measuring the time interval between a stimulating pulse applied to the atrium or ventricle of the heart and a responsive cardiac event, such as an atrial or ventricular depolarization or contraction, and means for using this measured time interval as a control parameter that adjusts the pacing rate of the pacemaker.

A further object of the invention is to provide such a pacemaker that further includes means for processing the previously measured time intervals (from the past several heart cycles) in order to generate a reference control parameter that smoothly and safely effectuates a pacing rate change.

A still further object of the present invention is to provide a system and method for accurately sensing the occurance of a paced P-wave within the heart, that is, for sensing the depolarization of the atrium immediately after delivery of an atrial pacing stimulus, or for accurately sensing the occurance of a paced R-wave immediately after delivery of a ventricular pacing stimulus.

The physiological sensor of the present invention is premised on the discovery that the time interval between application of a stimulating pulse to the atrium or ventricle of a heart and the resulting atrial depolarization or the ventricular depolarization (which ventricular depolarization could, in turn, be related to the depolarization that follows an atrial depolarization or that results from a ventricular stimulating pulse) varies as a function of the physiological need of the body within which the heart is located. In one embodiment, therefore, the sensor of the present invention measures the time interval between application of an atrial stimulation pulse, or "A-pulse," and the occurance of a responsive atrial depolarization, or "P-wave" (the occurrence of a P-wave indicating depolarization of the atrium). In this embodiment, the time interval measured is designated as the A-P interval, or API. In a second embodiment, available for use when AV conduction of the heart is not blocked, the sensor of the present invention measures the time interval between application of the A-pulse and the subsequent occurance of a ventricular depolarization or "R-wave" (the occurrence of an R-wave indicating depolarization of the ventricle). In the second embodiment, the time interval measured is designated as the A-R interval or ARI. In a third embodiment, primarily for use with a single chamber pacer that senses and pulses in the ventricle (or a dual chambered pacer programmed to operate only in a single chamber mode), the sensor measures the time interval between application of a ventricular stimulation pulse, or "V-pulse," and the occurrance of the responsive ventricular depolarization, or R-wave. In this embodiment, the time interval measured is designated as the V-R interval, or VRI. These and other embodiments of the invention may also measure other time intervals measured relative to the application of an A-pulse or V-pulse.

The physiological sensor of the present invention therefore includes time interval measurement means for measuring the A-P, A-R, V-R or other designated intervals. Preferably these interval measurements are smoothed, averaged, or otherwise processed through appropriate processing means to produce a reference interval measurement that is derived from the combined interval measurements of the past several heart cycles. As such, this reference interval measurement is free of abrupt changes, and any established trend in the lengthening or shortening thereof can be safely interpreted as a change in the physiological need of the body.

The pacemaker of the present invention includes a physiological sensor as above-described in combination with a pulse generator; means for delivering a stimulating pulse at a prescribed rate to a selected heart chamber; means for sensing a cardiac event, such as a P-event or an R-event; and means for adjusting the rate of the stimulating pulse as a function of the derived or reference interval measurement from the physiological sensor. In a demand-type pacemaker, wherein a stimulating pulse is provided by the pacemaker only when a natural cardiac event fails to occur within a prescribed escape time interval, the present invention adjusts the escape time interval as a function of the reference interval measurement, and thereby effectuates the same desired result of an adjustable pacing rate as a function of physiological need. These escape time intervals are typically subsets of the longer A-V interval, and V-A interval, the sum of which defines the pacing interval controlled by the pacemaker. Accordingly, the reference interval measurement can be used to adjust the pacemaker-controlled A-V interval, the V-A interval, or both the A-V interval and the V-A interval, thereby controlling the pacing rate. The reference interval measurement generated by the present invention may also be used to control other parameters associated with the operation of the pacemaker in order to render the pacemaker more physiologically responsive.

In accordance with one embodiment of the physiological sensor of the present invention, used in conjunction with an demand-type pacemaker, the A-P or A-R interval measurements are processed as follows:

At least three (3) previous heart cycles are monitored. If an A-pulse was inhibited more than once during the previous consecutive three (3) cycles, then the pacing rate does not change; if, however, at least 3 A-pulses have been generated and at least three API or ARI measurements have successfully been made, then the API or ARI measurements over these previous three cycles are examined to determine if all are less than or greater than a reference interval measurement, which reference interval measurement is representative of the current pacing rate. If an increasing or decreasing trend is noted, that is, if all three previous consecutive interval measurements are moving in the same direction, then the interval measurement closest to the reference interval measurement is used as the new reference interval measurement.

In another embodiment of the physiological sensor, the time interval measurements may be smoothed through averaging an appropriate number of measurements from prior cardiac cycles.

As is evident from the above, an important requisite for embodiments of the invention that measure the A-P interval is the ability to sense a paced P-wave or stimulated atrial depolarization. Conventional sensing of the P-wave using a bipolar lead, where the same bipolar lead has been used to stimulate the atrium, is not possible because the sensing amplifiers remain saturated at the time during which the P-wave occurs. Therefore, non-conventional P-wave sensing means must be employed. While various techniques may be used to sense such a P-wave, the preferred embodiment of the present invention contemplates a unipolar use of a conventional atrial-placed bipolar lead. In accordance with this technique, atrial stimulation occurs through unipolar exitation of the atrium through the distal tip of the conventional bipolar lead. P-wave sensing occurs through unipolar sensing, ring-to-case, of the P-wave generated by the atrium as depolarization occurs. Utilizing the spaced-apart distal tip and ring of the conventional bipolar lead in a unipolar mode of operation allows the P-event, occuring within a relatively short time after the generation of the A-pulse, to be accurately sensed. Alternatively, separate unipolar leads may be selectively placed within the atrium, spaced one apart from the other, in order to serve the same function. Further, for a single chamber pacer connected only to the ventricle, these same techniques may be used to sense the R-wave that occurs in response to an applied V-pulse.

BRIEF DESCRIPTION OF THE DRAWINGS

The above and other objects, features, and advantages of the present invention will be more apparent from the following more particular description thereof presented in conjunction with the following drawings, wherein:

FIGS. 15A-15E are further state diagrams as in FIGS. 14A-14C.

FIG. 19 shows frequency response curves for the P-wave sense/amplifier and the P-wave sensing amplifier.

DETAILED DESCRIPTION OF THE INVENTION

The following description is of the best presently contemplated mode of carrying out the invention. This description is not to be taken in a limiting sense but is made merely for the purpose of describing the general principles of the invention. The scope of the invention should be determined with reference to the attached claims.

Figure 1:
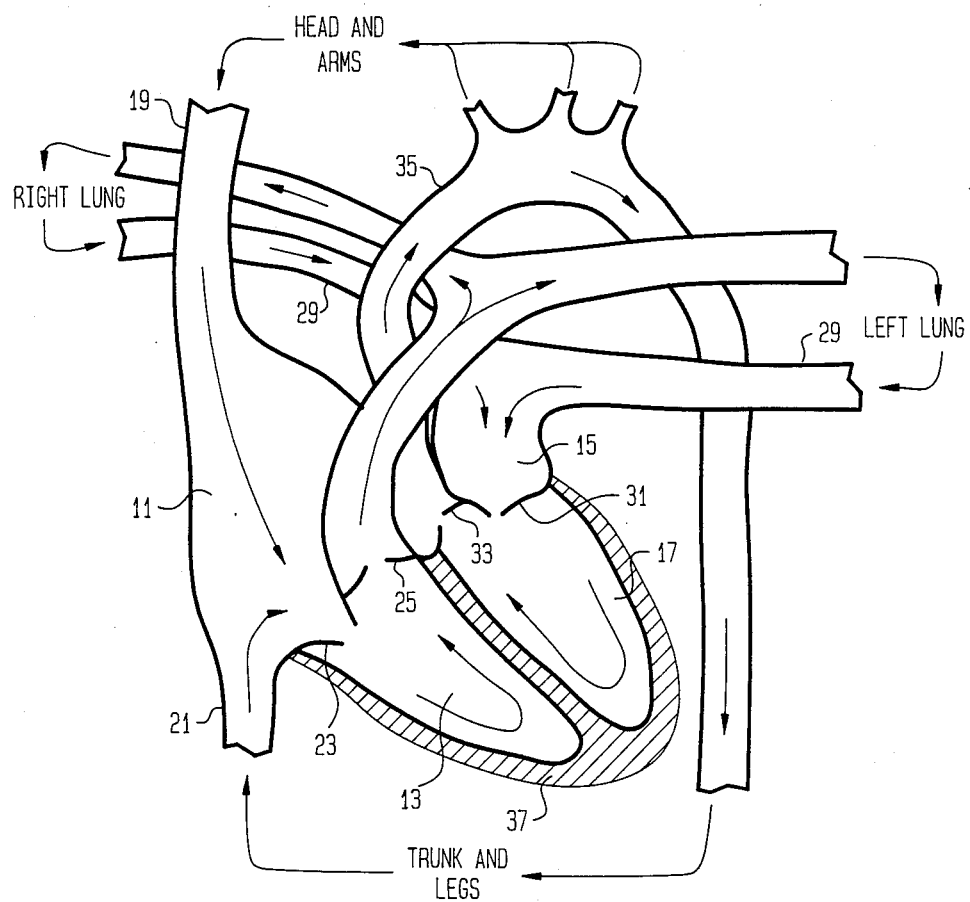
FIG. 1 is a schematic representation of a human heart illustrating the main components thereof and the flow of blood therethrough.

Before describing the present invention in detail, it will be instructive to briefly review some fundamental operating principles associated with pacemakers, especially dual-chamber demand-type pacemakers. To best understand the operations of such pacemakers, it is helpful to first have a basic understanding of cardiac anatomy. Accordingly, reference is made to FIG. 1 wherein is shown a schematic representation of the heart and the flow of blood therethrough. The heart is essentially made up of four (4) chambers; a right atrium 11, a right ventricle 13, a left atrium 15, and a left ventricle 17. The atrium chambers function primarily as reservoirs into which incoming blood is received, while the ventricles function primarily as pumping chambers to pump the blood away from the heart to a specific destination. Blood, carrying carbon dioxide waste from the body cells, enters the right atrium by way of the superior vena cava 19 or the inferior vena cava 21. At the appropriate time, the right atrium 11 contracts and pushes the blood through the tricuspid valve 23 into the right ventricle 13. A short time later, the right ventricle 13 contracts and pushes or pumps the blood through the pulmonary valve 25, which valve leads to the pulmonary artery 27. The pulmonary artery 27 divides into two branches, one leading to the right lung and the other leading to the left lung. At the lungs, the carbon dioxide in the blood is removed and replaced with fresh oxygen. The oxygenated blood returns from the lungs in the pulmonary vein 29, also divided into two branches, one branch for each lung, and is deposited in the left atrium 15. At approximately the same time that the right atrium 11 is contracting, the left atrium 15 also contracts and pushes the blood through the mitral valve 31 into the left ventricle 17. The left ventricle 17 contracts at approximately the same time as the right ventricle contracts and pushes or pumps the blood through the aortic valve 33 into the aorta 35. The aorta is the main artery that delivers the blood throughout the body. The natural rhythm of the heart thus includes the contraction of the atria, followed a short time later by the contraction of the ventricles. The ventricles do most of the work of the heart, as evidenced by the thickness of the heart muscle or myocardium 37 that surrounds both the right and left ventricles 13 and 17.

Figure 2:
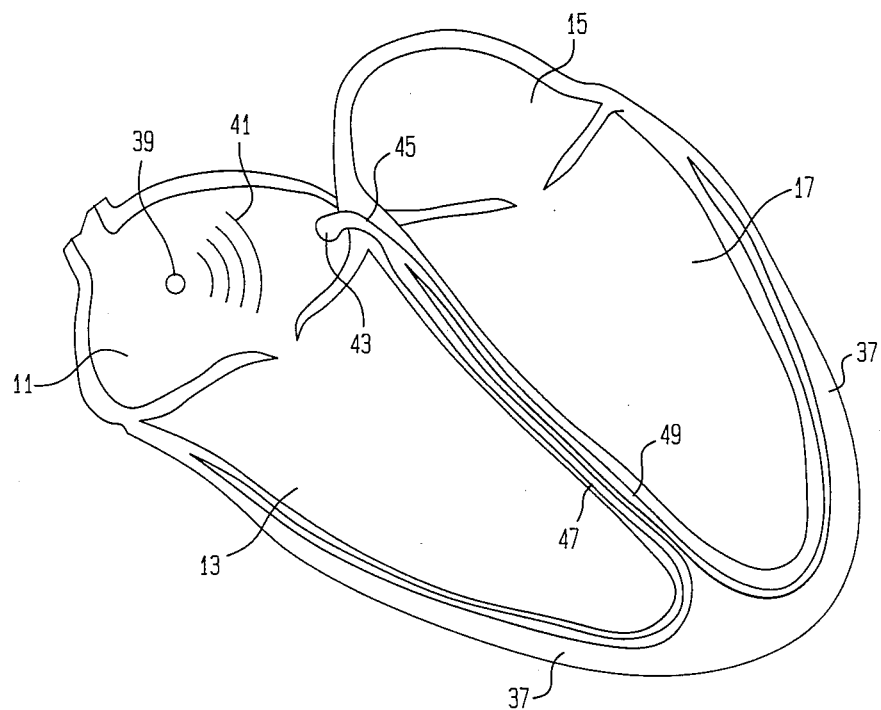
FIG. 2 is a simplified representation of the heart showing the location of the SA and AV nodes.

Referring next to FIG. 2, there is shown a simplified diagram of the heart showing the four (4) chambers thereof. For the sake of clarity, many of the elements associated with the heart have been omitted from the drawing of FIG. 2. Located in the right atrium 11 is an S-A node 39. The S-A node is often referred to as the heart's natural pacemaker. This is because the S-A node 39 begins the electrical impulse, depicted in FIG. 2 as the wavefront 41, that spreads in wave fashion to stimulate both the right atrium 11 and the left atrium 15. It is this electrical impulse 41 that causes the depolarization of the muscle tissue that forms the walls of the atria, thereby causing atrial contraction to occur. Also included in the right atrium is an A-V node 43. The A-V node 43 is stimulated by the electrical impulse 41 propagated from the S-A node 39. Upon stimulation, and after a short pause (typically about 0.1 seconds), the A-V node initiates an electrical impulse that starts traveling down an A-V bundle 45. After a short distance the A-V bundle 45 divides into a right bundle branch 47 and a left bundle branch 49. These left and right bundle branches distribute the electrical impulse throughout the myocardium or heart muscle 37, thereby causing the ventricles to depolarize and contract.

Figure 3:
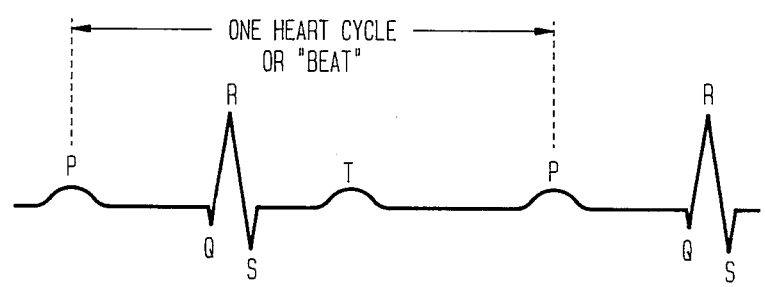
FIG. 3 is a timing diagram illustrating the normal, non-paced operation of the heart of FIG. 2 as sensed through conventional skin ECG electrodes or equivalent.

Shown in FIG. 3 is a representation of the various waveforms that are generated, as sensed by skin electrodes placed on the chest, in response to the above-described activities. A P-wave represents the depolarization of both atria. The QRS-wave, commonly referred as the QRS complex, represents the electrical impulse as it travels from the A-V node to the various fibers branching from the left and right bundle branches 47 and 49 as it is distributed into the myocardial cells, thereby causing ventricular depolarization. The T-wave represents the repolarization of the ventricles so that they may be stimulated again. (Note, repolarization of the atrium is usually not sensed because it occurs about the same time as the QRS complex, and any signals representative of atrial repolarization are therefore masked out by the QRS complex.) One cardiac cycle is represented by a P-wave, a QRS complex, and a T-wave. This cycle is repeated continuously as the heart pumps the blood as described in connection with FIG. 1. In summary, the P-wave represents depolarization of the atria. The QRS complex, sometimes referred to as simply an R-wave, represents the depolarization of the ventricles. Depolarization/contraction of the atria, followed a short time thereafter by depolarization/contraction of the ventricles, are the cardiac events that must occur if the heart is to efficiently perform its function as a pump in distributing blood throughout the body.

Figure 4:
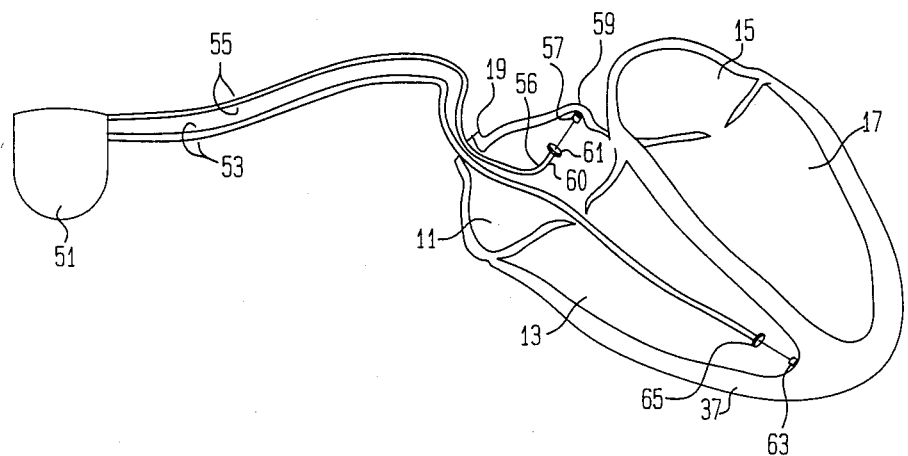
FIG. 4 is a simplified representation of the heart showing the manner in which a pacemaker is connected thereto through insertion of bipolar leads into both the right atrium and right ventricle.

Referring next to FIG. 4, there is shown a simplified representation of one way that an implanted pacemaker 51 may make electrical contact with the heart. FIG. 4 depicts the use of two (2) bipolar leads 53 and 55, each being directed into a separate chamber of the right heart. A bipolar lead comprises a single filar that includes two (2) electrically insulated conductors. For example, the lead 55 includes a first conductor 56 that is electrically connected to a distal tip 57 of the lead. This distal tip is typically placed in a cavity of the right atrium referred to as the atrial appendage 59. A known distance from the distal tip 57, an electrode ring 61 is electrically connected to the other conductor 60 of the bipolar lead 55. Similarly, a distal tip 63 and a conductive ring 65 are associated with the bipolar lead 53 that is placed in the apex of the right ventricle 13. The manner in which the leads 55 and 53 are inserted into the heart, as well as the manner in which the pacemaker 51 is implanted in the body of a patient, are well known in the art.

Figure 5:
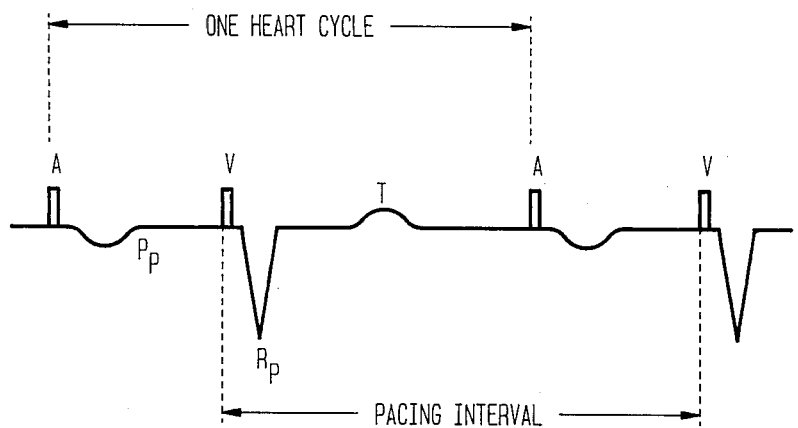
FIG. 5 is a timing diagram showing the relationship between pacing pulses delivered to the heart from a pacemaker and the heart's response to these pacing pulses.

FIG. 5, shows a timing diagram that illustrates the response of the heart to stimulation pulses that are generated by an implanted pacemaker, such as the pacemaker 51 shown in FIG. 4. In response to an atrium stimulation pulse, or A-pulse, delivered to the right atrium 11 through the distal tip 57 of lead 55 (FIG. 4), both atria contract and a P-wave is generated. Because the stimulating A-pulse originates from a different point within the right atrium than does the normal stimulating pulse from the S-A node 39 (FIG. 2), the P-wave generated in response to this A-pulse does not appear the same as a naturally occurring P-wave. For purposes of this application, this difference between a P-wave in response to an A-pulse and a P-wave in response to the naturally occurring pulse from the S-A node is depicted as a P-wave of opposite polarity. The waveform of FIG. 5 is further distinguished by referring to it as the $P_P$-wave, indicating that it is a paced P-wave, or a P-wave in response to a pacing signal. Similarly, in response to a stimulation pulse applied to the right ventricle, an R-wave is generated, represented in FIG. 5 as an inverted $R_P$ pulse. The R-wave in FIG. 5 is shown inverted from the R-wave shown in FIG. 3 because the stimulating pulse propagates through the ventricle chamber in a different direction than does the natural stimulating pulse that propagates through the left and right bundle branches. Hence, for purposes of this application, the natural responses or natural depolarizations of the heart are represented in the figures as a positive P-wave (a waveform going in the upwards direction) and a positive R-wave. Depolarizations of the atria or ventricles in response to an externally generated stimulation pulse, such as occurs with a pacemaker, are represented as a negative going $P_P$ wave or $R_P$ wave.

Figure 6:
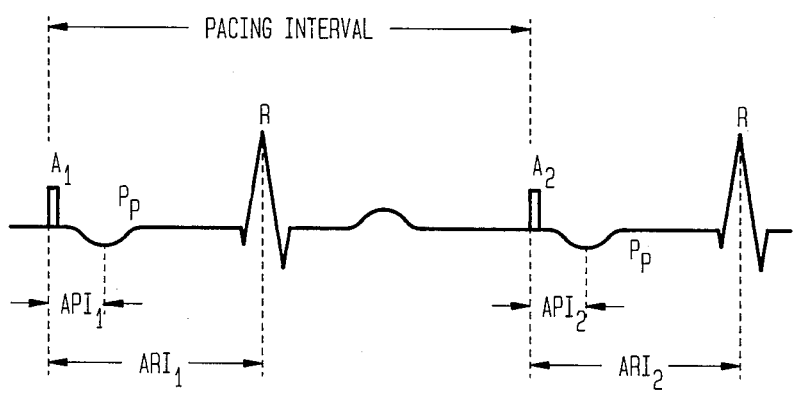
FIG. 6 is a timing diagram similar to FIG. 5 showing a P-wave that occurs in response to an atrium stimulation pulse, followed by a natural (non-paced) ventricular R-event, and further showing consecutive A-P and A-R time intervals that occur over consecutive pacing intervals.

With reference to FIG. 6, one possible response to an atrium stimulation pulse, A, is shown. As is seen in FIG. 6, in response to the pulse $A_1$, a $P_P$ wave form is generated a short time later, which time interval is identified as $API_1$ (referring to the first A-P interval). In response to the atria depolarization evidenced by the $P_P$ wave, and in the absence of A-V block, the ventricles depolarize and contract without the need of a stimulation pulse. Such depolarization occurs a time $ARI_1$ later (referring to the first A-R interval of the sequence shown in FIG. 6). At an appropriate time subsequent to the generation of the first atrium stimulation pulse $A_1$, a second atrium stimulation pulse, $A_2$, is generated by the pacemaker. In response to the $A_2$ stimulus, a second $P_P$ wave is generated a time $API_2$ after the generation of the $A_2$ pulse. Again, a naturally occuring R-wave occurs a time $ARI_2$ subsequent to the generation of the A2 pulse. The AP/AR intervals shown in FIG. 6, designated as $API_i$ and $ARI_i$, are time intervals that play a key role in connection with the preferred embodiment of the invention described herein. More particularly, it is changes in these time intervals, when sensed after monitoring the individual time intervals over a plurality of heart cycles, that indicate changes in the physiological need of the body within which the heart is located. Hence, this particular embodiment of the invention is concerned with measuring the AP/AR intervals, and in processing these measured intervals in such a fashion that the resulting processed measurement can be used to adjust the control parameters of the pacemaker in order to change the pacing rate thereof so that this pacing rate approximates the changes that would occur in a healthy (non-paced) heart in response to the same changes in physiological need.

Figure 7A:
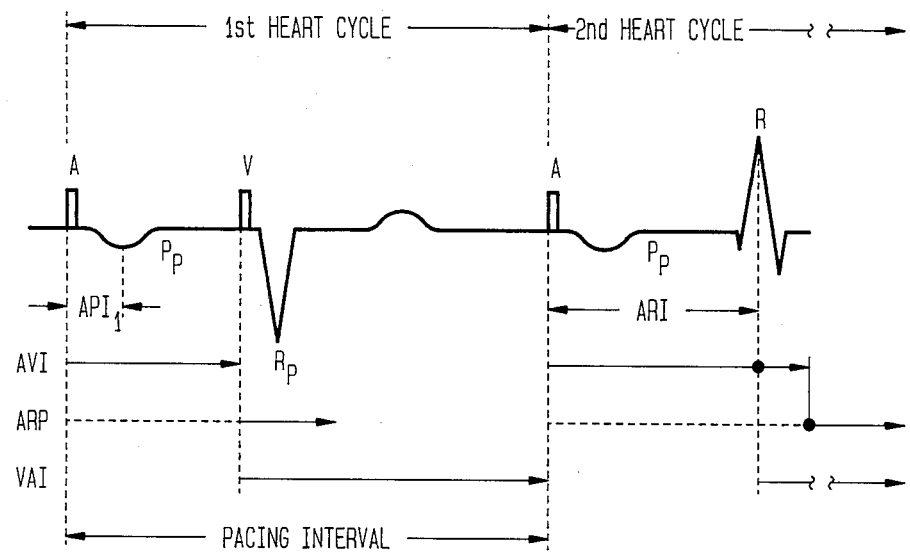
FIGS. 7A and 7B are timing diagrams as in FIGS. 5 and 6, but showing some different possible sequences of cardiac events and further defining various time intervals that are used in the operation of a dual-chamber demand-type pacemaker.
Figure 7B:
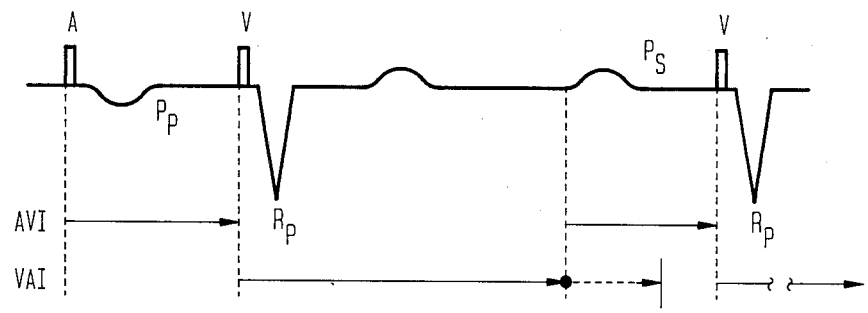

Referring next to FIGS. 7A and 7B there are shown further timing diagrams that define various intervals that are commonly used in controlling a dual-chamber demand-type pacemaker. The description that follows is somewhat simplified, but will be useful in understanding the operation of a dual-chamber pacemaker. Additional details associated woth a preferred pacemaker are described hereinafter in connection with FIGS. 14 and 15, and in Appendix B. In a demand-type pacemaker it is common to define an escape interval during which activity within the heart is sensed. If a natural cardiac event occurs during this escape interval, that is if a natural P-wave or R-wave is sensed, then a corresponding stimulating pulse need not be generated. Not only does this mode of operation allow the heart to function in its natural state, if it is able, but it also helps conserve the limited power stored within the battery of the pacemaker. In FIG. 7A, it is seen that both the AP interval and AR interval are illustrated as in FIG. 6. Also shown in FIG. 7A, however, is an AVI, or AV interval. This is a prescribed time set by the pacemaker during which a naturally occuring R pulse must occur, if one is to occur, prior to the generation of a ventricle stimulation pulse, V. As indicated in FIG. 7A, the AV interval has timed out for the first heart cycle shown, thereby causing the V-pulse to be generated. During the second heart cycle, however, the AV interval has not yet timed out at the point in time when the naturally occurring R-wave appears. Thus, there is no need for the pacemaker to generate a V stimulation pulse during the second heart cycle. Also illustrated in FIG. 7A is an atrial refractory period, or ARP. During this refractory period, the normal sensing mechanisms used within the atrium are nonresponsive. This refractory period is analogous to the natural refractory period of myocardial tissue immediately following depolarization and prevents the pacemaker from detecting any depolarization signals or noise that might result in timing errors. The refractory period is made up of two components, the absolute refractory period (indicated by the dashed line), during which detection of all signals is blocked, and a noise sampling or relative refractory period (represented by the solid line) during which detected signals are evaluated for a repetitive rate. As will be evident from the discussion that follows, the atrial refractory period, or ARP, does not prevent the detection of a $P_P$ pulse because, as previously stated, this pulse is detected using a sensing means different from the normal atrial sensing probe.

Also shown in FIG. 7A is a VA interval, or VAI. The beginning of this interval is initiated by the generation of a V-stimulation pulse, or the sensing of a natural R-wave. This VA interval, less the ARP, defines the time during which a natural (non-paced) P-wave must be detected if the A stimulation pulse is to be inhibited. As is evident from FIG. 7A, the pacing interval or rate set by the pacemaker is equal to the VA interval, VAI, plus the AV interval, AVI. Hence, by varying or adjusting these two time periods, the pacing interval of the pacemaker can be controlled, thereby controlling the heart rate.

Referring next to FIG. 7B, a different cardiac event sequence is illustrated. In this figure, it is seen that an A-pulse, or atrial stimulus, is first generated, causing a $P_P$ wave (or atrial depolarization) to occur. The AV interval is initiated by the generation of the A-pulse. At the conclusion of the AV interval, a V-pulse or ventricle stimulation pulse is generated because no natural occuring R-wave was sensed prior to that time. In response to the generation of the V-pulse, the ventricle depolarizes as evidenced by the $R_P$-wave, and the next VA interval is initiated. Before the VA interval, or VAI, terminates, however, a natural P-wave (identified as P, and sometimes referred to as a sinus P-wave) occurs. Accordingly, there is no need for the pacemaker to generate an atrium stimulation pulse. The sensing of the P wave re-initiates the AV interval. During this interval, the sensors in the ventricle are monitoring the ventricle activity to determine if a naturally occuring R-wave is present. For the situation shown in FIG. 7B, a naturally occurring R-wave does not occur prior to the termination of the AVI, so a V-pulse is generated, thereby causing a paced $R_P$ wave to occur, indicating ventricular contraction.

It is to be understood that FIGS. 7A and 7B represent simplified timing diagrams that illustrate only two of a very large number of heart event sequences that can occur. Volumes have been written by those skilled in the art describing the various heart rhythms, and abnormalities related thereto, that may occur. While most modern pacemakers are designed to recognize and deal with many of these abnormalities, a description of such matters herein would add little to the understanding of the present invention. In fact, a detailed description of all the heart rhythms and abnormalities associated therewith could obfuscate an understanding of the present invention. Accordingly, no such detailed description will be presented herein beyond that which is believed necessary to fully understand the present invention.

At this point it would be helpful, however, to review the different type of pacemakers that are available, and with which the present invention could be used. Generally, pacemakers are identified by a three letter code. The first letter represents the chamber of the heart that is paced. This letter may be a V for ventricle, an A for atrium, or a D for double (meaning that both the ventricle and atrium are paced). The second letter indicates the chamber sensed. Again the possible letters used are the V for ventricle, and A for atrium, a D for double, or the number "0" for none. The third letter indicates the mode of response of the pacemaker. A "T" indicates a triggered mode of response wherein the pacemaker regularly sends a stimulation pulse to the heart. An "I" indicates an inhibited mode of response, indicating that a stimulation pulse will be delivered to the heart unless it is inhibited by a naturally occurring cardiac-event that occurs within a predefined time interval. A "D" indicates a double mode of response, wherein the pacemaker may either operate in a triggered or inhibited mode. It is contemplated that the third letter could also be used to indicate the addition of the physiological sensor of the present invention to the pacemaker. For example, if the third letter were a "P", for "physiological", then that could be used to signal a multimode response pacemaker that includes automatic pacing interval adjustments in response to the second change in physiological need. Hence, a VVP pacer could be one in which the ventricular chamber is paced, the ventricular chamber is sensed, and the V-R interval is measured and used as a controlling parameter to automatically adjust the pacing interval in accordance with the teachings of the present invention. A DDP pacemaker, in accordance with this marking scheme, would be the most versatile of all modern pacemakers. This is because such a pacemaker could not only be programmed to operate in any mode that is best suited for the particular patient, but it would also automatically adjust the pacing interval in accordance with the sensed physiological need of the patient, regardless of the chamber or chambers of the heart that are being paced or sensed. While there are several DDD pacemakers currently available on the market, such as the AFPII 283 manufactured by Pacesetter Systems, Inc. of Sylmar, Calif., none are yet available that include the sensing and adjustment capabilities of the present invention. However, it is to be understood that the present invention—a physiological sensor that can be used to automatically adjust the pacing rate delivered or controlled by a pacemaker—could be adapted for use with any of the existing or yet to be designed pacemakers.

There are essentially three operating modes or types of pacemakers that are presently envisioned for use with the physiological sensor of the present invention. These are:
1. A single chamber atrial pacemaker;
2. A single chamber ventricular pacemaker; and
3. A dual-chamber pacemaker.

A single chamber atrial pacemaker would measure the A-P interval and use this measurement to adjust the pacing interval in an appropriate direction. A single chamber ventricular pacemaker would measure the V-R interval and use this measurement to adjust the pacing interval in an appropriate direction. A dual chamber pacemaker could measure either the A-P interval, the V-R interval, or the A-R interval, depending upon its mode of operation, and use these measurements to adjust the pacing interval in an appropriate direction. Because the dual chamber pacemaker is the most versatile, and because the single chamber pacemakers are really subsets of the dual chamber pacemaker (at least insofar as an understanding of the present invention is concerned), the description that follows is directed towards a dual chamber pacemaker. However, it is to be emphasized that the present invention is not so limited. Moreover, where the description given hereinafter refers to the measurement of the A-P interval, it is to be understood that these same teachings could be applied in measuring or describing the V-R interval.

Figure 8:
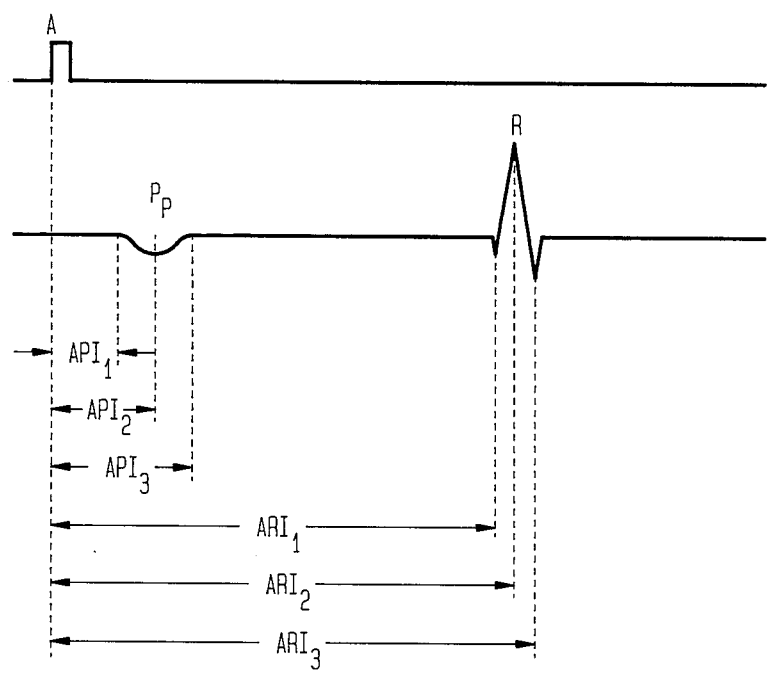
FIG. 8 is a timing diagram with an expanded time base that illustrates variations of the A-P/A-R interval time measurements that may be utilized as part of the invention.

Referring next to FIG. 8, there is shown a timing diagram having an expanded time base illustrating some variations of the A-P and A-R time intervals that could be utilized with the present invention. Because the paced P-wave is not a sharp pulse as are the stimulation pulses, such as the A-pulse, it may be advantageous to terminate the A-P interval at various points on the $P_p$ wave. For example, as illustrated in FIG. 8, the API could terminate at the commencement of the paced P-wave, at the peak of the paced P-wave, or at the conclusion of the paced P-wave. As a practical matter, the detection circuitry is the simplest and less costly if the peak of the P-wave is used as the detection point. Moreover, because there may be variations in the sensing circuitry, the peak of the P-wave may not be consistently sensed, but some threshold on the P-wave will be sensed with sufficient consistency for a meaningful API measurement to be made. Likewise, the ARI measurement will typically be made to the peak of the R-wave, designated as $ARI_2$ in FIG. 8, because this is the easiest signal to detect. However, assuming that appropriate detection circuitry is available, the leading edge, designated $ARI_1$, or the trailing edge, designated $ARI_3$, could be used in place of the peak ARI measurement. Similarly, a detection circuit that senses the maximum slew rate of the R-wave could be employed.

Figure 9A:
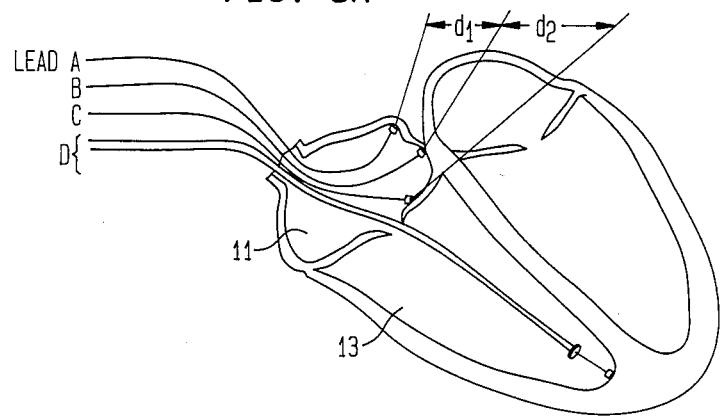
FIG. 9A is a simplified representation of the heart showing how a plurality of unipolar leads could be positioned within the atrium chamber of the heart for use with the present invention as an alternative to the atrial bipolar lead shown in FIG. 4.
Figure 9B:
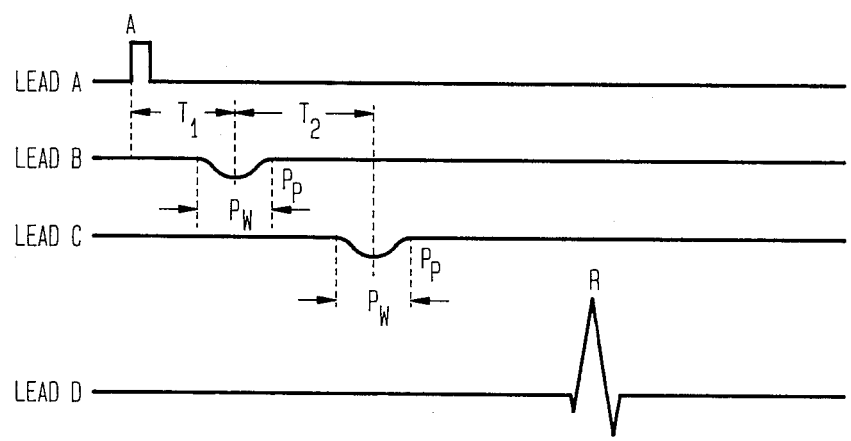
FIG. 9B is a timing diagram illustrating the sequence of P-waves that are sensed using the unipolar leads of FIG. 9A.

Next, referring to FIG. 9A, there is shown an alternative embodiment of lead placement within the heart that could be used with the present invention. In accordance with this embodiment, a plurality of unipolar leads, identified as leads A, B, and C, may be selectively placed within the atrium 11 of the heart. A conventional bipolar lead, identified as lead D, is shown as being inserted in the ventricle 13 of the heart. In accordance with the embodiment shown in FIG. 9A, it is contemplated that the atrium stimulation pulse, or A-pulse, would be delivered to the heart through lead A. The tip of lead B, being spaced a fixed distance from lead A, would sense the generation of the P-wave at a certain time later, identified as $T_1$ in the timing diagram of FIG. 9B. The time $T_1$ is a function of the propagation rate of the stimulation pulse as this stimulation pulse travels the distance $d_1$ in FIG. 9A. As described thus far, it is noted that the tip of lead B in FIG. 9A is performing the same function as the ring electrode 61 of the bipolar lead 55 in FIG. 4. A third lead, lead C, could also be employed, with its tip spaced a distance $d_2$ from the tip of lead B. Hence, as indicated in FIG. 9B, the $P_p$ wave sensed by lead C would be delayed by an amount equivalent to the propagation delay time of the stimulation pulse through the atrium as it travels the distance $d_2$. It is within the scope of the present invention that either the times $T_1$, $T_2$, $T_1-T_2$, or $T_1+T_2$, could be used as the timing interval that is measured in order to determine changes in physiological need in accordance with the present invention. It is also contemplated that changes in the width of the paced P-pulse, PW, could be used to indicate physiological need. Further, while FIG. 9A illustrates unipolar leads placed in the atrium, and a bipolar lead placed in the ventricle, it is to be understood that other combinations of unipolar/bipolar leads, all unipolar leads, or all bipolar leads (FIG. 4) could be employed. Further, a tripolar lead having at least two spaced-apart ring electrodes in addition to a distal tip electrode could be used to achieve the function described above.

Figure 10:
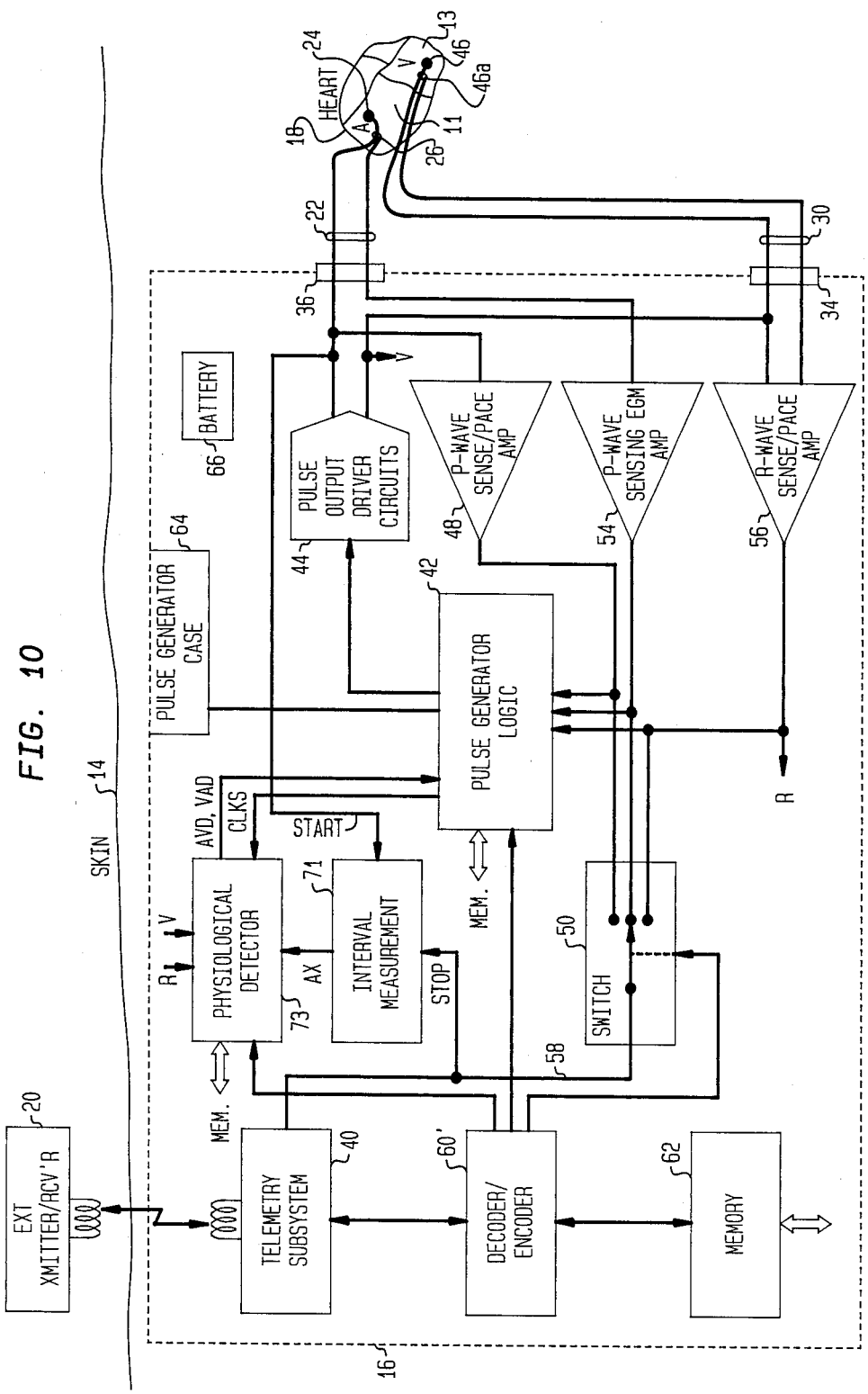
FIG. 10 is a block diagram of the pacemaker system of the present invention.

Referring now to FIG. 10, a block diagram of an implanted pacemaker 16 according to the invention is shown, the pacemaker 16 being connected to a user's heart 18. At appropriate times, the pacemaker 16 my be electromagnetically in contact with a telemetry transmitter and receiver 20 external to the user's skin 21. A conventional bipolar atrial lead 22 is provided having a first or tip electrode 24 at its distal end and a second electrode 26 spaced apart from the tip electrode 24 and in the configuration of a typical bipolar lead ring electrode. It may be understood that a second ring electrode and an associated amplifier may be used for greater signal strength in sensing the electrical activity in the atrium. The tip electrode 24 is located in contact with atrial tissue of the heart atrium 11. A bipolar ventricle lead 30 is located in the heart ventricle 13 and is attached to the pacemaker 16 through a ventricular connector 34. Of course, a unipolar ventricle lead could also be used. The atrial lead 22 is connected to the pacemaker 16 through an atrial connector 36. The pacemaker 16 includes a telemetry subsystem 40 for transmitting data and parameter values to the external telemetry transmitter and receiver 20, and for receiving data instructions and the like from the external telemetry transmitter and receiver 20. The pacemaker 16 also includes pulse generator logic circuitry 42 which, in turn, controls pulse output driver circuits 44 for providing both atrial and ventricle stimulation pulses. The atrial output of the pulse output driver circuits 44 is connected through the atrial connector 36 to the atrial tip electrode 24 for stimulation of the atrium; the ventricle output of the pulse output circuits 44 is connected through the ventricle connector 34 to a ventricle tip electrode 46 for stimulation of the ventricle. A P-wave sense/pace amplifier 48 having bandpass characteristics as explained below is also connected through the atrial connector 36 to the atrial tip electrode 24 for receiving electrical signals present at the electrode 24. The output of the P-wave sense/pace amplifier 48 is also connected to the pulse generator logic circuitry 42 and to switch 50, the purpose of which will be explained below. The implanted pacemaker, in operating as a "demand" type pacer, would not provide stimulation to the atrium when amplifier 48 provides at its output a signal indicating the sensing of an intrinsic or sinus P-wave. A second amplifier, a P-wave sensing EGM amplifier 54 having bandpass characteristics as explained below has its input connected through the atrial connector 36 to the second atrial electrode 26. The output of the P-wave sensing amplifier is also connected to the switch 50. An R-wave sense/pace amplifier 56 is also provided, its input being connected to the pulse output driver circuits 44, the ventricle tip electrode 46, and a ventricle ring electrode 46a, these last two connections being made through the ventricle connector 34. The output of the R-wave sense/pace amplifier 56 is connected to the pulse generator logic circuitry 42 for inhibiting a ventricle stimulation pulse in the presence of spontaneous ventricular activity, (i.e., in the presence of a naturally occuring, non-paced, R-wave) and to the switch 50. Amplifier 56 has a sufficiently broad band-pass characteristics to pass electrical signals of substantially all native (intrinsic) ventricular activity. The output of the switch 50 is connected via a line 58 to the telemetry subsystem 40 for real time transmission of the output of either the P-wave sense/pace amplifier 48, the P-wave sensing amplifier 54 or the R-wave sense/pace amplifier 56. The specific amplifier output to be transmitted is selected by the physician via instructions transmitted by the external telemetry transmitter and receiver 20 and received by the implanted telemetry subsystem 40. These instructions are decoded by a decoder and encoder 60'. The output of the decoder and encoder 60' is utilized to establish which amplifier output 48, 54 or 56 is to be connected to the telemetry system 40 for transmission to the external telemetry transmitter and receiver 20.

Although the switch 50 is shown as a switch, it should be readily apparent that any kind of selectable connecting means could be employed to provide continuity between one of the amplifiers 48, 54 and 56 and the line 58. Further, two or more of the amplifier outputs could be transmitted simultaneously if proper provisions were made within the telemetry subsystem 20. In addition, a memory 62 is provided which receives parameter information from the decoder and encoder 60', this parameter information being utilized to control the pulse generator logic circuitry 42. The tip electrode 24 for stimulating the atrium and the tip electrode 46 for stimulating the ventricle may be utilized in a unipolar configuration with the return path being provided through a conductive portion of the pulse generator case 64 which is connected to the pulse output driver circuits 44. Alternatively, bipolar operation may be employed where the return path is through the conductor connected to the ring electrode, although such bipolar operation may make sensing of a $P_p$-wave difficult, as explained below. A battery 66 is also incorporated for providing power to the implanted pacemaker 16. It should also be recognized that although an implanted pacemaker is shown for illustrative purposes, the invention is in no way limited to an implanted pacemaker. An external pacemaker could also be provided in accordance with the teachings of the invention. Further, although bipolar atrial and ventricular leads were chosen for illustrative purposes, a unipolar ventricular lead could also have been utilized provided appropriate connectors were available on the pacemaker, and a plurality of unipolar leads could have been used within the atrium as shown in FIG. 9. Similarly, a multi-conductor atrial lead could be provided with two of the conductors providing a bipolar atrial lead and the third conductor being connected to the P-wave sensing ECG amplifier 54 shown in FIG. 10.

Also included in the pacemaker 16 is an interval measurement circuit 71 and a physiological detector 73. The interval measurement circuit 71 comprises an appropriate time interval measurement circuit. The time interval measured is started by the generation of an atrium stimulation pulse as generated by the pulse output driver circuits 44, and is stopped by the output of either the P-wave sensing EGM amplifier 54 (which output indicates the sensing of a $P_p$ wave), or the output of the R-wave Sense/Pace amplifier (which output includes the sensing of an intrinsic R-wave). The interval measurement circuit therefore measures the ARI or the API, as selected by control signals received through the telemetry subsystem. Further, it is contemplated that one mode of operation could include always measuring the ARI, is present, but if not present, as for example in a situation where heart block exists, then automatically reverting to measuring the API.

The time interval measured by the interval measurement circuit 71 is passed to the physiological detector 73, which detector 73 processes the measured interval as described more fully below and generates appropriate control parameters as a result of this processing that are delivered back to the pulse generator logic 42.

The manner in which the implanted pacemaker 16 operates will now be explained. This explanation will be given in two parts, a first part of which relates to the sensing function of the pacemaker, and a second part of which relates to the physiological detecting function of the pacemaker and the manner in which the pacing rate is varied or controlled as a result of this physiological detection. Because the telemetry functions and pulse generator/pulse delivery functions are conventional functions performed by pacemakers known in the art, no further explanation of these functions will be presented herein.

Sensing Function

Figure 16A:
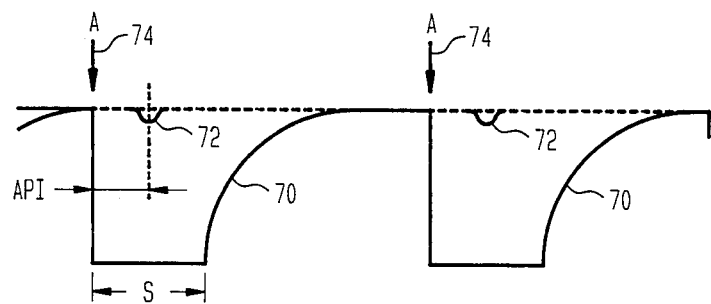
FIG. 16A is a waveform diagram illustrating the problem of P-wave detection utilizing the atrial stimulation electrode as the P-wave sensing electrode.

First, with reference to the sensing function of the pacemaker, operation of the pacemaker 16 shown in FIG. 10 can be best understood by reference to FIGS. 16A, 16B, 17A and 17B. One of the problems associated with atrial pacing is determining whether atrial or P-wave capture has been effected by atrial stimulation pulses. This involves sensing the occurrence of a paced $P_p$ wave. In prior art systems, the sensing circuit corresponding to the P-wave sense/pace amplifier 48 in FIG. 10 sensed signals present at the electrode at the lead distal end (corresponding to the tip electrode 24 in FIG. 10). Referring now to FIG. 16A, the voltage present at the output of the P-wave sense/pace amplifier 48 in the presence of an atrial stimulation pulse corresponds in general to the waveform shown at 70. Thus, the output of the P-wave sense/pace amplifier 48 is saturated during the period "S" shown in FIG. 16A. Because the paced $P_p$-wave voltage is small with respect to the saturation voltage caused by the A stimulation pulse, which $P_P$-wave is represented in FIG. 16A by the wave 72, it is difficult, if not impossible, to pick out the time at which the $P_p$ wave occurres relative to the stimulation pulse A, which A-pulses occur at the times indicated by the arrows 74. Because of this difficulty in determining when the $P_p$-wave 72 actually occurred relative to stimulation pulse occurrence as shown at 74, it is difficult for the physician to determine if the stimulation pulse has effected P-wave capture. It is also difficult, if not impossible, to measure the API as is required by the present invention.

Figure 16B:
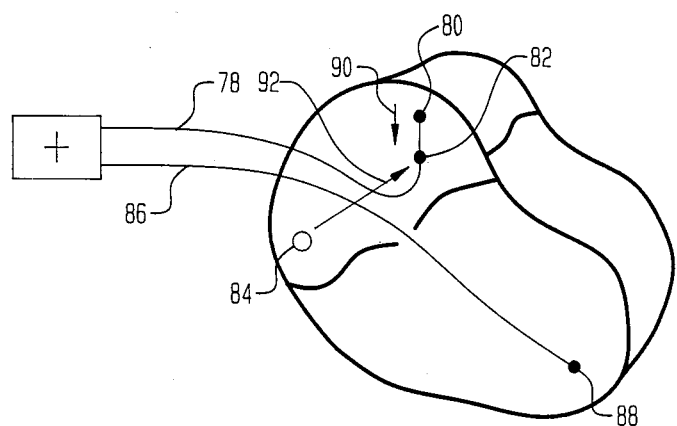
FIG. 16B is a schematic representation of a user's heart showing locations of the atrial and ventricle electrodes.

Referring now to FIG. 16B, a simplified representation of the heart is shown, showing a pacemaker 76 according to the invention, having a conventional atrial lead 78 and, also having a stimulation and sensing electrode 80 at its distal end and a second or $P_p$-wave sensing electrode 82 spaced apart from the stimulation electrode 80. By way of example only, the atrial lead 78 is configured in the form of a J at its distal end so that the stimulation electrode 80 can be located within the atrial appendage (not shown). The heart sinus node 84 is also shown, as well as a ventricle lead 86 having its stimulation electrode 88 located in the ventricular apex. It can be appreciated that the further the sensing electrode 82 is spaced-apart from the stimulation electrode 80, the less the stimulation pulses will interfere with $P_p$-wave sensing by the sensing electrode 82. This is because the electrical stimulation signal, by the time it propagates to the sensing electrode 82, has decreased in amplitude a sufficient amount to preclude it from interfering with the sensing of the $P_P$ wave. However, it should be apparent that the sensing electrode 82 cannot be so far removed from the stimulation electrode 80 that it would no longer be within the heart atrium. For the embodiment shown, all electrodes 80, 82 and 88 use the case of the pacemaker 76 as a return electrode, the case being positive with respect to a negative going pulse present at both stimulation electrodes 80 and 88. Another advantage of utilizing the spaced-apart sensing electrode 82 for $P_p$-wave detection is that the P-wave electrical characteristics as picked up by the sensing electrode 82 differ because of the direction of propagation. This is shown by the arrows 90 and 92, arrow 90 showing the propagation direction from the stimulation electrode 80 and arrow 92 showing the propagation direction from the sinus node 84. As explained previously, this propagation direction is what causes the polarity of the two signals to be different. Further, in determining P-wave capture, this allows the physician to determine if the P-wave occurred as a result of spontaneous atrial activity or stimulated atrial activity. Moreover, because of the different distances between the sensing electrode 82, the sinus node 84, and the stimulation electrode 80, it can be appreciated that even if the sinus code 84 is operating in synchronism with the stimulation pulses, the known propagation time between a stimulation pulse and P-wave generation could be used to determine if P-wave generation were due to spontaneous or stimulated atrial activity. Further, it can be appreciated that although a typical bipolar atrial electrode 78 is utilized, all three electrodes 80, 82 and 88 operate in a unipolar manner in that they all use the pacemaker 76 case as a common return electrode. Alternatively, the ventricular lead 86 could be a bipolar lead, and the sensing/pacing in the ventricle could be operated in a bipolar manner without interferring with the P-wave detection in the atrium.

Figure 17A:
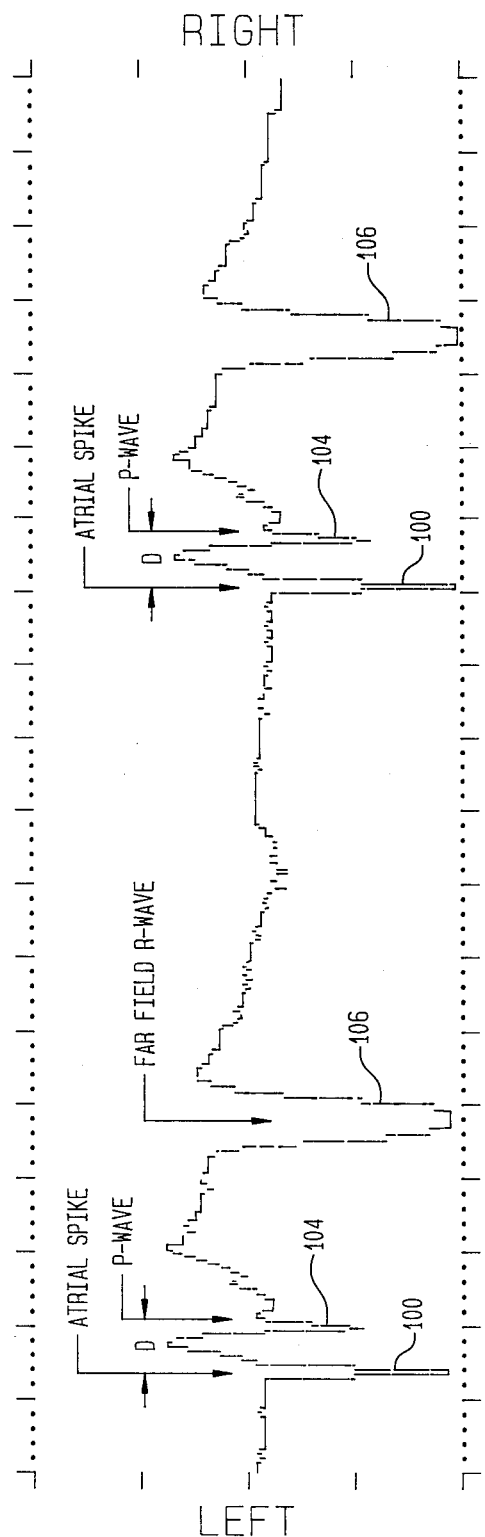
FIGS. 17A and 17B are waveform diagrams of intercardiac electrogram (EGM) signals, FIG. 17A illustrating an EGM signal showing P-wave capture and FIG. 17B illustrating an EGM signal in the absence of P-wave capture.
Figure 17B:
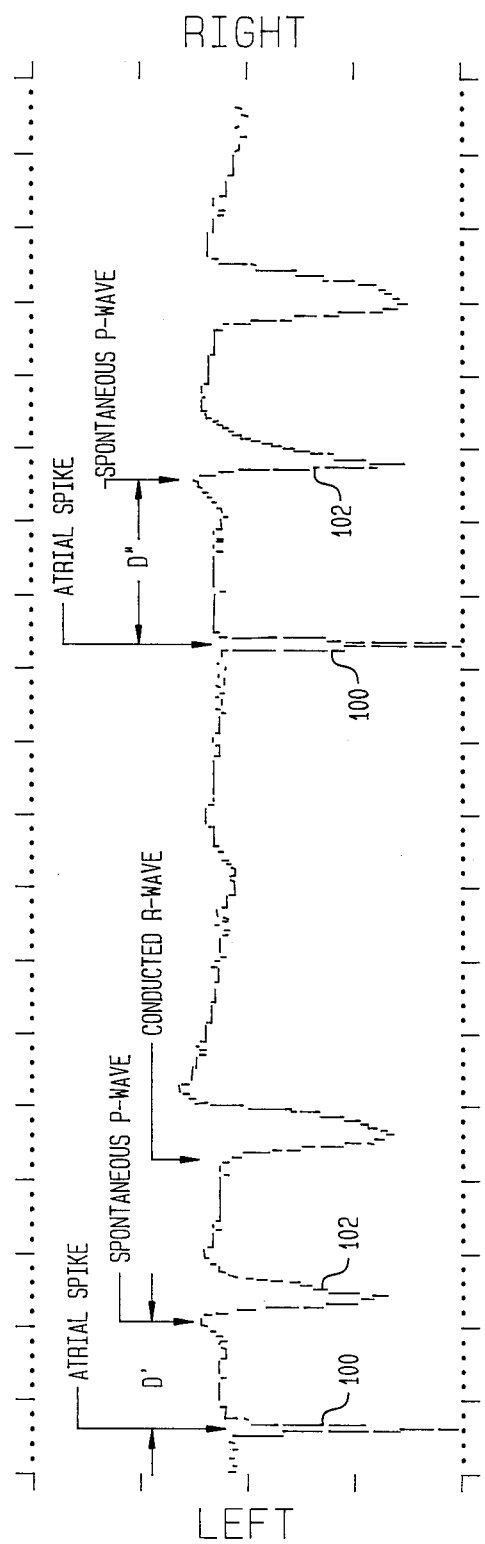

Detection of atrial capture can be further understood in reference to FIGS. 17A and 17B, which figures show actual intercardial electrograms as sensed by an implanted pacemaker and transmitted to a suitable display device. Referring to FIG. 17A, atrial stimulation pulses 100 can be seen. Further, P-waves 104 and R-waves 106 can also be seen. The time differential D between atrial stimulation and P-wave occurrence in successive cycles can be seen to be constant. Thus, the physician can assume that P-wave capture as a result of the atrial stimulation pulses has occurred provided that the distance D corresponds approximately to the propagation delay due to the distance between the stimulation electrode 80 and the sensing electrode 82 as explained in conjunction with FIG. 16B. Referring now to FIG. 17B, the time differentials D' and D" between the atrial stimulation pulses 100 and P-wave occurrences 102 can be seen to be different. Thus, the physician can conclude the P-wave capture by the atrial stimulation signals has not occurred but that the P-waves are spontaneous or "native" or "intrinsic" in origin. Under normal circumstances with respect to FIG. 17B, the physician would assume that the magnitude of the stimulation pulses is below the stimulation threshold of the particular patient's atrium and would accordingly increase their magnitude until P-wave capture occurred, that is, until an EGM signal similar to that shown in FIG. 17A is observed. Again, in prior art systems, it would be impossible to observe the presence of P-waves utilizing the stimulation electrode 80 (FIG. 16B) as the sensing electrode due to the saturation of the P-wave sense/pace amplifier resulting from the atrial stimulation pulse (see FIG. 16A).

Figure 18:
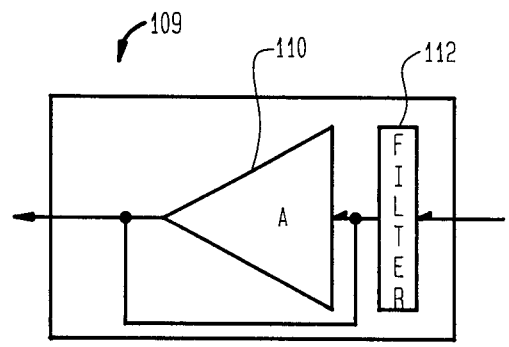
FIG. 18 is a block diagram of a P-wave amplifier as shown in FIG. 10.

FIG. 18 shows a simplified block diagram of a typical P-wave or R-wave wave amplifier 109 such as those shown in FIG. 10 as blocks 48, 54 and 56. The amplifier 109 includes an amplification portion 110 and an input filter 112. The difference between the P-wave sense/pace amplifier 48 and the P-wave sensing amplifier 54 is in the bandpass characteristics of the amplification portion 110 and filter 112 combination. The amplitude and bandpass characteristics of the P-wave sense/pace amplifier 48 as chosen to provide to the pulse generator logic circuitry 42 a positive indication of P-wave occurrence in the absence of an atrial stimulation pulse, while at the same time rejecting non-P-wave signals such as far-field R-wave signals and muscle electrical noise. This is to allow the pulse generator logic circuitry 42 to determine if the atrium is operating spontaneously or whether an atrial stimulation pulse is required. It is the output of this amplifier 48 that is subjected to the atrial refractory period discussed previously.

The purpose of the P-wave sensing amplifier 54 (FIG. 10) is to provide an electrogram of all, or most all, atrial electrical activity including an indication of $P_p$-wave occurrence in the presence of an atrial stimulation pulse. Thus, the precise characteristics of the $P_p$-wave and its location with respect to an atrial stimulation pulse must be determinable in order to measure the AP interval and in order to determine if the P-wave is occurring spontaneously or is occurring as a result of an atrial stimulation pulse.

In order to meet these different requirements, the amplifier 110 and filter 112 combination of the P-wave sense/pace amplifier 48 as shown in FIG. 10 can be chosen to have a center frequency at 60 Hz and 3 db points at approximately 10 Hz and 100 Hz. The purpose of this U-shaped frequency response is to maximize detection of the intrinsic P-wave which has a large frequency component near 60 Hz and to reject other signals such as some of that from the heart R-wave which by the time it reaches the atrium has lower frequency components and muscle electrical noise which has mostly higher frequency components. Thus, the bandpass characteristics of the P-wave sense/pace amplifier 48 must be chosen to attenuate all electrical signals within the atrium other than the frequencies that most characterize the intrinsic P-wave. Of course the bandpass characteristics described above are only representative of one embodiment, and other response characteristics could be chosen. For example, a response curve having a peak of between 40 Hz and 80 Hz and the 3 db points could lie between 0.1 Hz and 500 Hz could be chosen. The teaching of the invention merely is that the P-wave sense/pace amplifier 48 be chosen to pass signals characteristic of the intrinsic P-wave while tending to reject signals that are not characteristic of the intrinsic or sinus P-wave. Thus peak detection circuitry in the pulse generator logic circuitry 42 (FIG. 10) can be triggered by the output of the P-wave pace/sense amplifier 44 without danger of a false detection due to other electrical activity in the atrium.

The P-wave sensing EGM amplifier 54 is chosen to have a response that is essentially flat between about 3½ Hz and 200 Hz. This is to allow the $P_p$-wave to be sensed and to allow the physician to see all electrical atrial activity for a complete understanding of the atrial electrical environment including any T-wave ventricle signals and any farfield R-wave signals that are present. However, the invention is in no way limited to a $P_p$-wave sensing EGM amplifier 48 having a flat response, and a frequency response such as that of the P-wave sense/pace amplifier could also be utilized. In particular, use of such a frequency response that improves the ability to make the necessary AP interval measurement would be desired.

The above can be further understood by referring to FIG. 19. Here the P-wave sense/pace amplifier response 113 and the P-wave sensing EGM amplifier response 114 can be seen. As can be seen, the response 113 is chosen to pass the P-wave frequency and attenuate the frequencies associated with other physiologic events as shown at 115 and 116 in order to provide a relatively high amplitude output corresponding only to R- and P-wave events. The response 114 is chosen to pass all frequencies in order to provide an accurate overall EGM signal to the physician. As shown, response 114, of the sensing amplifier includes T-wave ventricular frequencies and far-field signals. If inclusion of these signals makes it difficult to accurately measure the AP interval, then a narrower response, such as is indicated by the dashed-line response 115' could be employed.

Figure 20:
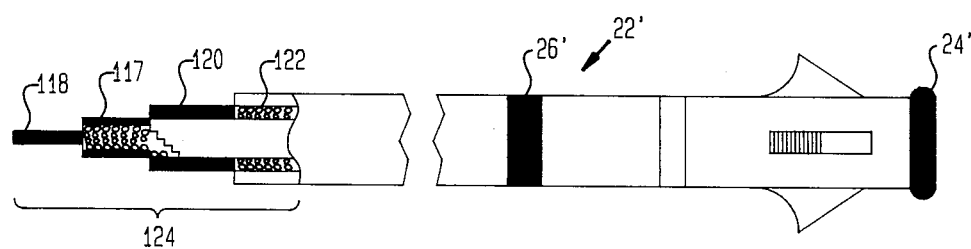
FIG. 20 is a partially cut-away atrial electrode of the type utilized in the embodiment of FIG. 10.

Referring now to FIG. 20, a lead 22' of the type shown in FIG. 10 as 22 is illustrated. Although a straight shank lead is shown for illustrative purposes, it should be recognized that a typical atrial-J lead could be utilized in the application shown in FIG. 10, and thus a portion of the distal end of the lead could be J-shaped. The lead 22' includes a tip electrode 24' which is connected through a spirally-wound conductor 117 to a first terminal 118. A ring electrode 26' is attached through a spirally-wound conductor 122 to a second terminal 120, this conductor 122 being electrically isolated from the conductor 117 attached to the tip electrode 24'. The terminals 118 and 120 are adapted to connect to appropriate connectors in the pacemaker. Although the connector or terminal arrangement generally shown at 124 is a typical in-line type of connector, other connector arrangements could be utilized such as having each terminal coming out of the proximal end of the lead to form a Y-shaped connector. The ring electrode 26' is spaced apart from the tip electrode 24' a distance such that when the tip 24' is located in the atrial appendage, the ring electrode 26' will also be located within the atrium. As previously explained, FIG. 20 merely illustrate a typical bipolar atrial lead which is utilized in the FIG. 10 embodiment while having its tip electrode and ring electrode operate in a unipolar fashion. Thus, an implantable pacemaker configured according to that shown in FIG. 10 can be utilized with conventional bipolar atrial leads without requiring a special purpose lead to be utilized.

Physiological Detecting Function

The second part of the manner in which the implanted pacemaker 16 (FIG. 10) operates will now be explained. This part relates to the physiological detecting function of the pacemaker and how the pacing rate is varied or controlled as a result of this physiological detection. Referring back to FIG. 10, the interval measurement circuit 71 can be realized using any suitable counting circuit that is started and stopped in the manner previously described. This counting circuit may be clocked by an appropriate high frequency signal (not shown) that is derived from the system clock used within the pulse generator logic 42. Once an interval measurement is made, this measurement is directed to the physiological detector 73.

Figure 11:
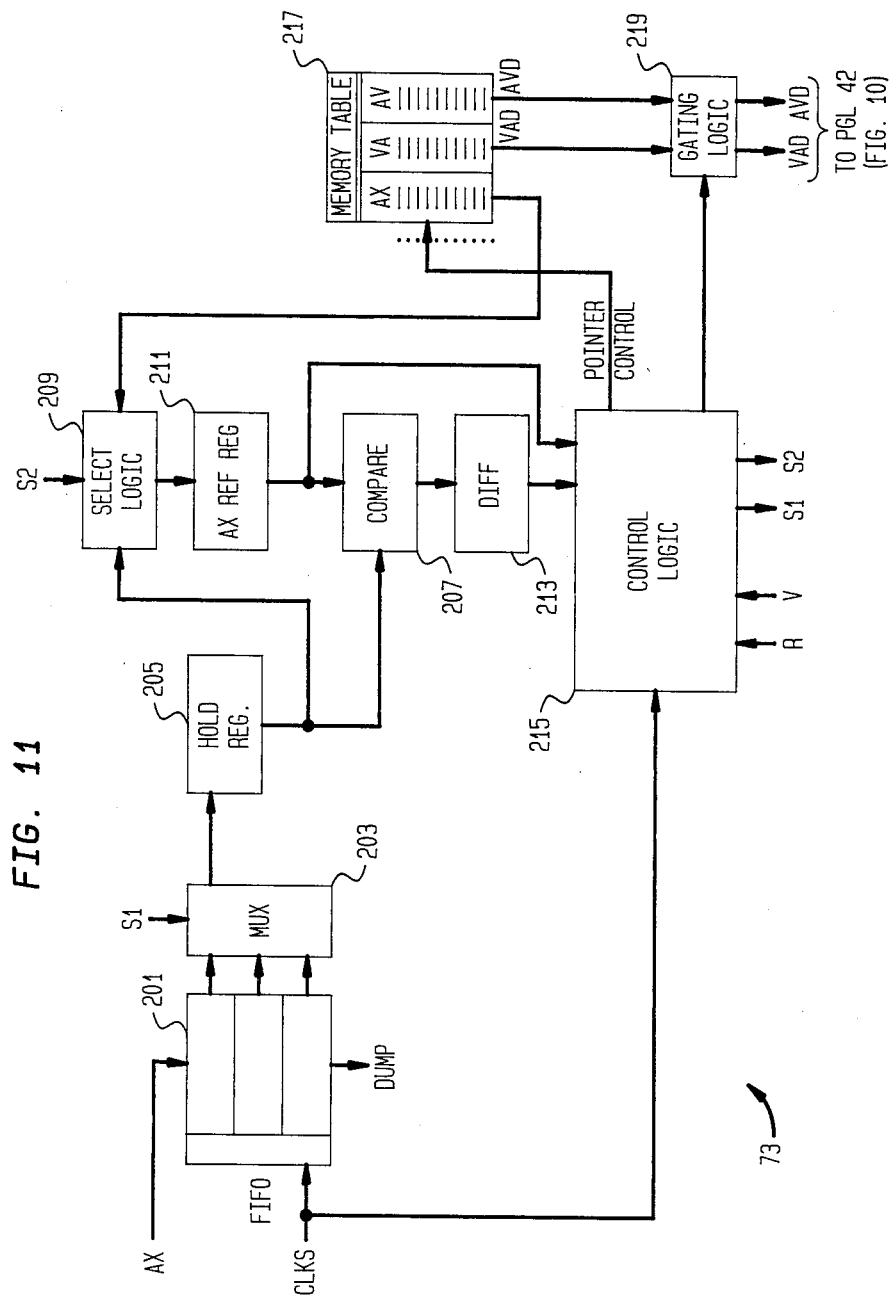
FIG. 11 is a block diagram of the physiological detector of FIG. 10.

Referring next to FIG. 11, there is shown a block diagram of a hardwave implementation of the physiological detector 73 of FIG. 10. As an alternative, the function performed by the detector 73 shown in FIG. 11 could be realized using a microprocessor that is controlled by a program stored in ROM (read only memory) or in RAM (random access memory). An advantage of using RAM is that program optimization for a particular patient is possible using telemetric transfer of data via link 40 in FIG. 10. Such an alternative embodiment is briefly described in Appendix A, attached hereto. As indicated previously, the interval measurement circuitry 71 of FIG. 10 measures the A-P interval, the A-R interval, or (for single chamber ventricular pacing) the V-R interval. For purposes of the discussion that follows in connection with FIGS. 11 and 12, this interval measurement will be generically referred to as the A-X interval measurement, where X refers to either the P (for the A-P interval measurement) or the R (for the A-R interval measurement), and where it is understood that the V-R measurement is processed similar to the processing of the A-X measurement, and where it is understood that a V-R measurement is included within the "A-X" designation for purposes of the description that follows.

The A-X interval measurement is loaded into a first-in, first-out, or FIFO register 201. The sequencing of the A-X value through FIFO 201 is controlled by clock signals, such as a clock corresponding to the pacing interval obtained from the pulse generator logic 42 (FIG. 10). Any signal that occurs during every heart cycle, such as the A-V delay, or AVD signal, could be used for this purpose. The FIFO 201 includes the capacity to hold at least three A-X interval measurements. Each measurement thus held in accessible through a multiplexer 203, the output of which is directed to a holding register 205. The contents of the holding register 205 may be directed to a comparison circuit 207 or through select logic 209 to an A-X reference register 211. The comparison circuit 207 compares the contents of the holding register 205 with the contents of the A-X reference register 211 and sends the difference between the value stored in these two registers to a difference register 213. The contents of the difference register 213 are available to control logic 215, as are the contents of the A-X reference register 211. Also included as part of the physiological detector 73 is a memory table 217. While the memory table 217 is shown in FIG. 11 as actually being inside of the physiological detector 73, it is understood that this memory table could also be located within the memory circuits 62 shown in FIG. 10. Stored within the memory table are a range of values for the A-X interval. Corresponding to each of these stored values is a corresponding value for the V-A delay, or VAD, and the A-V delay, or AVD. As will be described below, the VAD and AVD comprise the principal timing elements of the AV and VA intervals, which intervals define a pacing interval. Accordingly, by adjusting the values of the VAD and AVD, the pacing interval delivered by the pacemaker to the heart can be controlled. The control logic 215 includes pointer control circuitry that allows it to scan the A-X values stored in the Memory Table 217. The stored value of A-X at any given point or location within the memory table 217 may be transferred through select logic 209 to the A-X reference register 211. Similarly, the VAD and AVD values corresponding to the A-X value that is addressed through the pointer control of the control logic 215 can be delivered through appropriate gating logic 219 to the pulse generator logic 42.

Figure 12A:
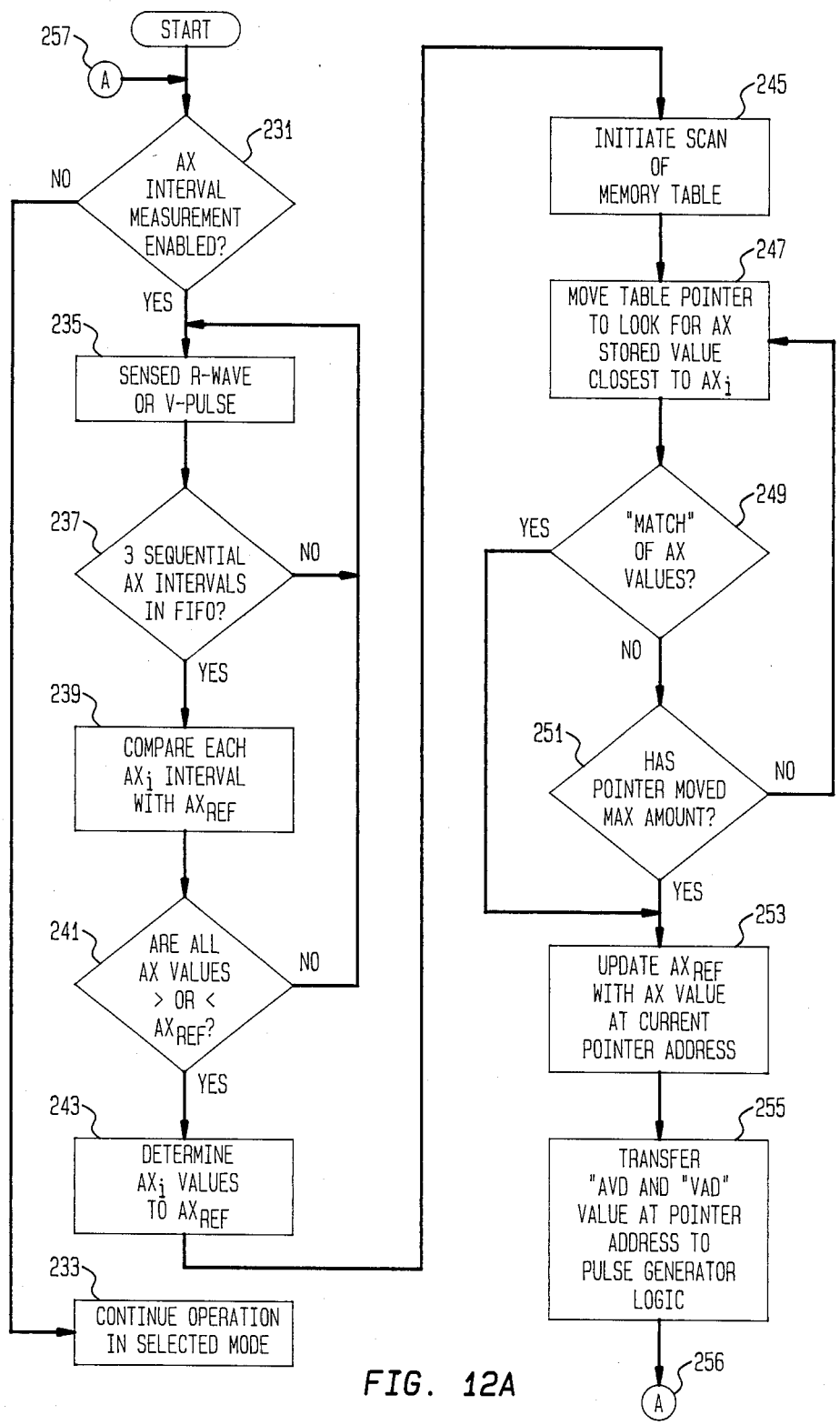
FIG. 12A is a flow diagram illustrating the process used by the control logic of FIG. 11 in converting the time interval measurement to control parameters for delivery to the pulse generator logic.

The operation of the detector 73 shown in FIG. 11 is best understood with reference to the flow diagram of FIG. 12A. This flow diagram defines the functions performed by the control logic 215. Referring to FIG. 12A, one of the first steps performed by the control logic 215 is to determine if the A-X interval measurement operating mode is enabled. This occurs at decision block 231. As will be discussed hereinafter, it is contemplated that other operating modes will be available with the pacemaker within which the present invention is utilized. Accordngly, if the A-X interval measurement is not enabled, then the pacemaker continues to operate in whatever other mode has been selected, as indicated in block 233 of FIG. 12A. If the A-X interval measurement has been enabled, then the next event that must occur for operation of the present invention is the sensing of an R-wave or a V-pulse, as indicated in processing block 235 of the flow diagram of FIG. 12A. (Note with reference to FIG. 10 that V and R inputs are shown going into the physiological detector 73. These inputs come from the pulse output driver circuits 44 and the R-wave sense/paced amplifier 56 respectively.) Once an R-wave or V-pulse has been sensed, then a determination is made as to whether three consecutive A-X intervals are present in the FIFO 201 (FIG. 11). This decision is indicated at decision block 237 of the flow diagram of FIG. 12. Should it be determined that three sequential A-X intervals are not present, then no further action is taken until the next R-wave or V-pulse is sensed. If, however, the FIFO 201 does contain three sequential A-X intervals therein, then each A-X interval, designated as A-$X_i$, is compared with the A-X value stored in A-X reference register 211. This A-X reference value is designated in FIG. 12 as A-$X_{Ref}$, and this comparison occurs at block 239 of the flow diagram of FIG. 12A. If this comparison indicates that all of the A$X_i$ values are greater than the A-X reference value, or if the comparision indicates that all of the A-$X_i$ values are less than the A-$X_{Ref}$ value, then an A$X_i$ trend has been established for purposes of the process shown in FIG. 12A. Determination of this trend, if present, is indicated at block 241 of the flow diagram of FIG. 12A. It is noted that if the trend is not present, then no further action is taken until the next R-wave or V-pulse is sensed, as indicated at block 235. If, however, a trend has been established at decision block 241—that is, all of the values of A$X_i$ are either less than or greater than the value of A-$X_{Ref}$—then a determination is made as to which A-$X_i$ value is closest to the A-$X_{Ref}$ value held in the A-X reference register 211 (FIG. 11), as indicated at block 243 of FIG. 12A. Once the A$X_i$ value closest to the A-$X_{Ref}$ value has been determined, this value is held in the holding register 205 while the pointer control of the control logic 215 begins to scan the memory table 217. As indicated previously, if an A-X value stored in the Memory Table 217 is addressed by the pointer control of the control logic 215, this value may be transferred through the select logic 209 and held in the A-X reference register 211. With the stored A-X value from the Memory Table 217 now in the A-X register 211, and the A$X_i$ value held in the holding register 205, the comparison circuitry 207 can again be used to determine the difference between the two values. If the values are not within a prescribed difference of each other, then the pointer control moves the table pointer in order to look for another value of A-X that is closer to the selected A value held in holding register 205. The steps of initiating scan of the Memory Table and moving the table pointer as above described are indicated at blocks 245 and 247, respectively, of the flow diagram of FIG. 12A.

Should the comparison of the stored A-X values and the selected A-$X_i$ value indicate a "match", as indicated at decision block 249 of FIG. 12A, (wherein "match" indicates that one value is within a prescribed difference of the other value, such as 2 percent), then the stored A-X reference value being held in the A-X reference register 211 remains held therein, as indicated at block 253 of FIG. 12A, and the corresponding AVD and VAD values at the current pointer address are transferred to the pulse generator logic 42, as indicated at block 255.

Because it is desirable that the pacing rate as controlled by the pacemaker not change too rapidly, a rate smoothing function is also employed in connection with the present invention. For purposes of this rate smoothing function, it is contemplated that the A-X values stored in the Memory Table 217 be stored in ascending or desending order. Thus, as the pointer control accesses various addresses within the Memory Table 217, it will look at gradually increasing or gradually decreasing values of A-X. To perform the rate smoothing function, a limit is placed on the number of increments that the control pointer may move at any one time. This action limits the amount or the rate at which the VAD and AVD values may change. Accordingly, at decision block 251 in FIG. 12A, a determination is made as to whether the pointer control has moved a maximum amount. If not, then the pointer may be moved one more address in order to look at the next value of A-X that is stored within the Memory Table 217. If the maximum movement of the pointer control has occurred, however, then further scanning of the memory table is terminated, and the A-X value stored at the then current pointer address is used as the updated $A-X_{Ref}$ value to be held in the A-X reference register, and the corresponding value of VAD and AVD are transferred to the pulse generator logic. In this fashion, the maximum rate at which the pacing interval (as set by the VAD and AVD values) may change can be controlled. Advantageously, this rate can be controlled whether it is increasing or decreasing. Moreover, through prescribing a different limit as the maximum amount which the pointer control may move as a function of whether the rate is increasing or decreasing, a hysteresis effect may be achieved.

Figure 13A:
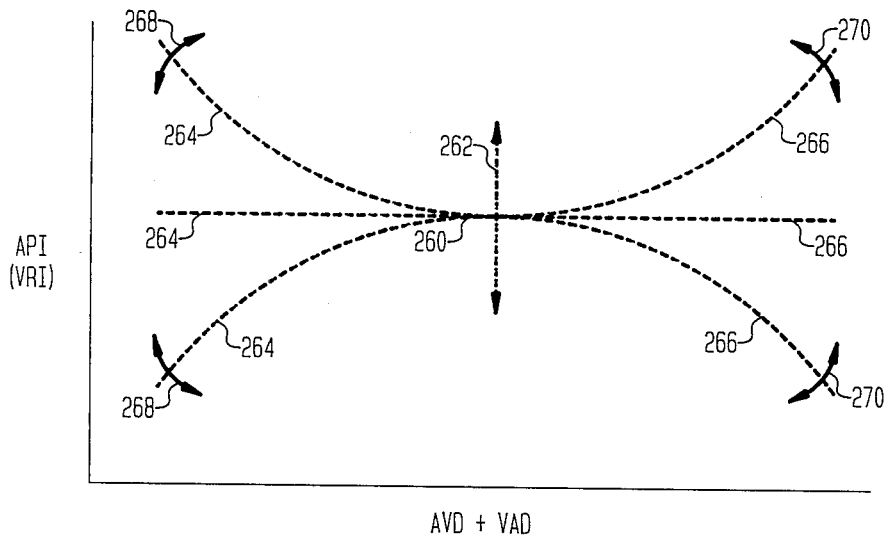
FIGS. 13A and 13B are graphs depicting illustrative relationships between the A-P and A-R intervals and the AVD and VAD (A-V delay and V-A delay) control parameters that could be established by the present invention.
Figure 13B:
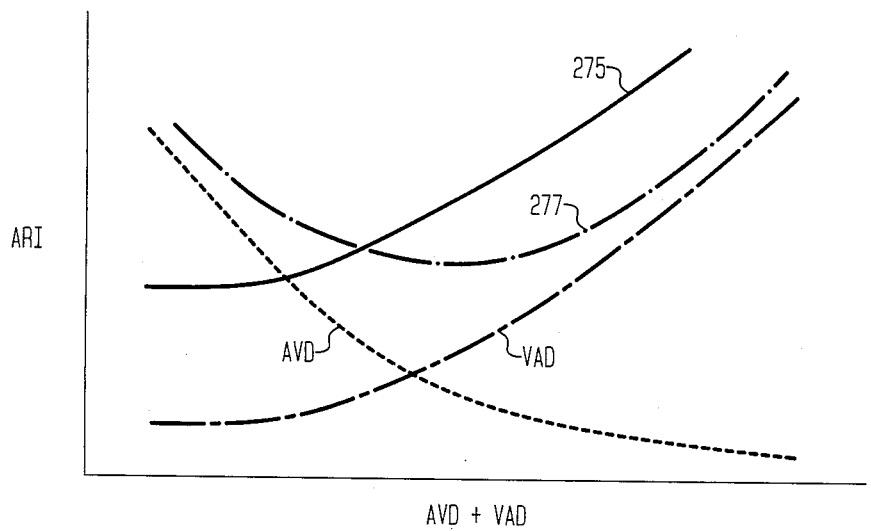

Referring next to FIGS. 13a and 13b, there are shown some illustrative graphs indicating some illustrative relationships between the API/ARI measurements and the corresponding AVD+VAD control parameters that may be programmed into the Memory Table 217. in FIG. 13a, it is seen that there may be a nominal AVD-+VAD value corresponding to a measured and processed API value, as indicated by the line 260. This value may, of course, be programmed to move up or down vertically as a function of the particular patient, as indicated by the arrow 262. The left and right ends 264 and 266, respectively, of the line 260 may be programmed to bend up or down, as indicated by the arrows 268 and 270. In this fashion, any particular relationship desired may be programmed to exist between API and AVD+VAD. In FIG. 13b, some possible relationships between the AR interval and the corresponding AVD+VAD pacing interval are also illustrated. A typical relationship may be as shown by line 275. However, because both the AVD and VAD values are stored in the Memory Table 217, it would be possible to program one to have an inverse relationship with respect to the measured ARI interval and the other to have a direct relationship, resulting in a pacing interval relationship as indicated by the dashed single-dot, line 277. As indicated previously, preliminary experiments indicate that the API measurement is increasing (getting longer) with increased workload on the patient. That is, as the heart rate needs to increase, the measured A-P interval is increasing. Because of the preliminary nature of these experiments, and the small number of samples that have been employed, further studies are being conducted. It is to be emphasized that the present invention is not limited to a particular relationship (increasing or decreasing) between the measured interval and the physiological needs of the patient. Rather, the present invention recognizes that there is a change in the measured API or ARI as this physiological need changes.

While the preferred embodiment of the physiological sensor of the present invention processes the measured A-X intervals in the manner described above, it is to be understood that other processing techniques or methods could be employed. For example, a simple moving average of the A-X intervals over a prescribed number of previous most recent consecutive cardiac cycles could be used in order to generate a smoothed reference A-X value. Alternatively, concurrent measurements of the AP and AR intervals could be compared to measurements of the PR interval (the time interval between a P-wave and an R-wave), and these various interval measurements could be compared one with another. Appropriate ratios, or relative changes between these measurements, could then be used to indicate a change in physiological need.

At least one embodiment of the invention includes compensation means for taking into account any artificially induced change in the A-X interval as a result of a change in pacing rate. That is, increasing or decreasing the rate at which an A-pulse is applied to the atrium, or a V-pulse is applied to the ventricle, may likely have some effect on the resultant A-P-, A-R, or V-R intervals, regardless of any change in physiological need. This pacing-induced change in these time intervals can be measured for a given patient, and then compensation made therefor as a particular physiological profile of the patient is programmed into the Memory Table 217. For example, suppose a patient having an implanted pacemaker has a measured AP interval of 50 msec while the patient is at rest, and that the patient's heart rate is 70 ppm (pulses per minute). The pacemaker rate can be programmably increased by an attending physician until the patient's heart rate has increased to 100 ppm, while the patient is still at rest. At a "resting" 100 ppm, the AP interval could again be measured. Suppose it has increased to 60 msec. Next, the patient exercises an appropriate amount and the AP interval is again measured, and at an "exercised" 100 ppm, the AP interval is measured to be, for example, 70 msec. The net difference between the "resting" 100 ppm AP interval and the "exercise" 100 ppm AP interval (i.e., 10 msec) would be the interval amount change that is properly attributable to physiological need, not the gross change in AP interval (i.e., 20 msec.) from the 70 ppm "resting" rate to the 100 ppm "exercise" rate. It is this net difference, personalized for each patient, that is, in accordance with one embodiment of the invention, acted upon by the processing circuitry in order to determine true physiological need. Typically, compensation for the pacer-induced changes in the interval periods can occur by subtracting or adding a pre-determined number to the measured interval as a function of the pacer-interval, (i.e., heart rate), which pre-determined number can be calculated for each patient by the physician through some simple tests and measurements as described above.

Figure 12B:
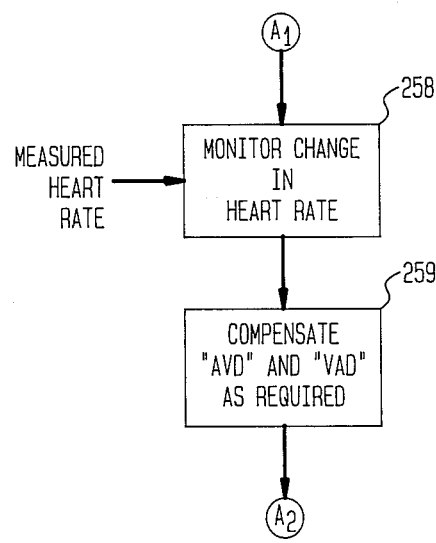
FIG. 12B is an extension of FIG. 12A for one embodiment of the invention.

FIG. 12B illustrates how the above described compensation technique could be included in the flow diagram of FIG. 12A. In FIG. 12B, the connecting A1 circle is intended to connect with the connecting circle 256 at the bottom of FIG. 12A, and the connecting A2 circle in FIG. 12B is intended to connect with the connecting circle 257 near the top of FIG. 12A. The extended process shown in FIG. 12B includes a process step 258 for tracking any changes in the measured heart rate (measured by sensing the occurrence of P and R events through the pacer electrodes); and a process step 259 for compensating the stored AVD and VAD values by an appropriate amount (which could be stored in a separate section of the Memory Table). Alternatively, compensation of AVD and VAD could be performed externally prior to storing the AVD and VAD values in the Memory Table. Such a preprogrammed compensation is preferred if sufficient data can first be obtained from the patient.

Figure 14A:
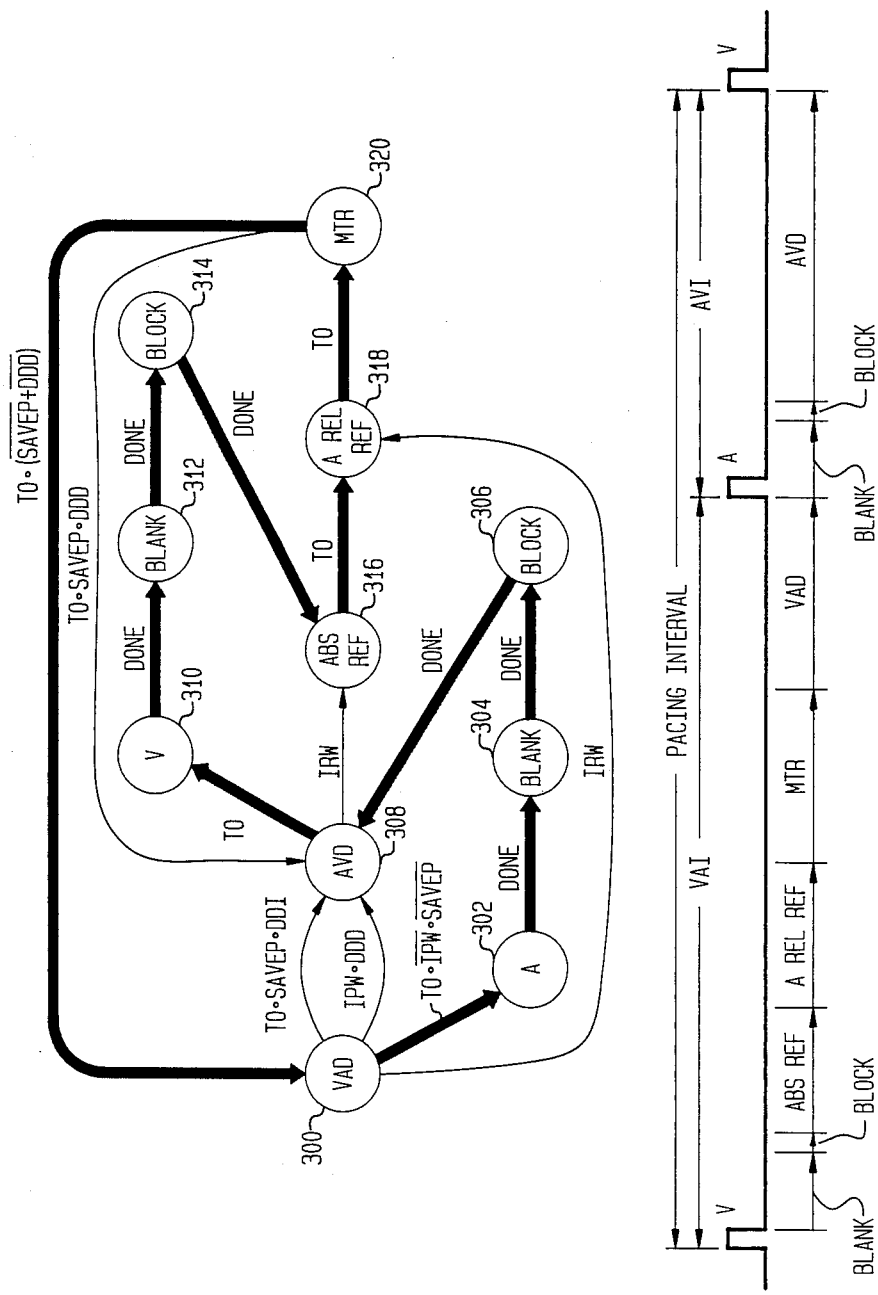
FIGS. 14A-14C are state diagrams illustrating possible operating states associated with the pulse generator logic of FIG. 10.
Figure 14B:
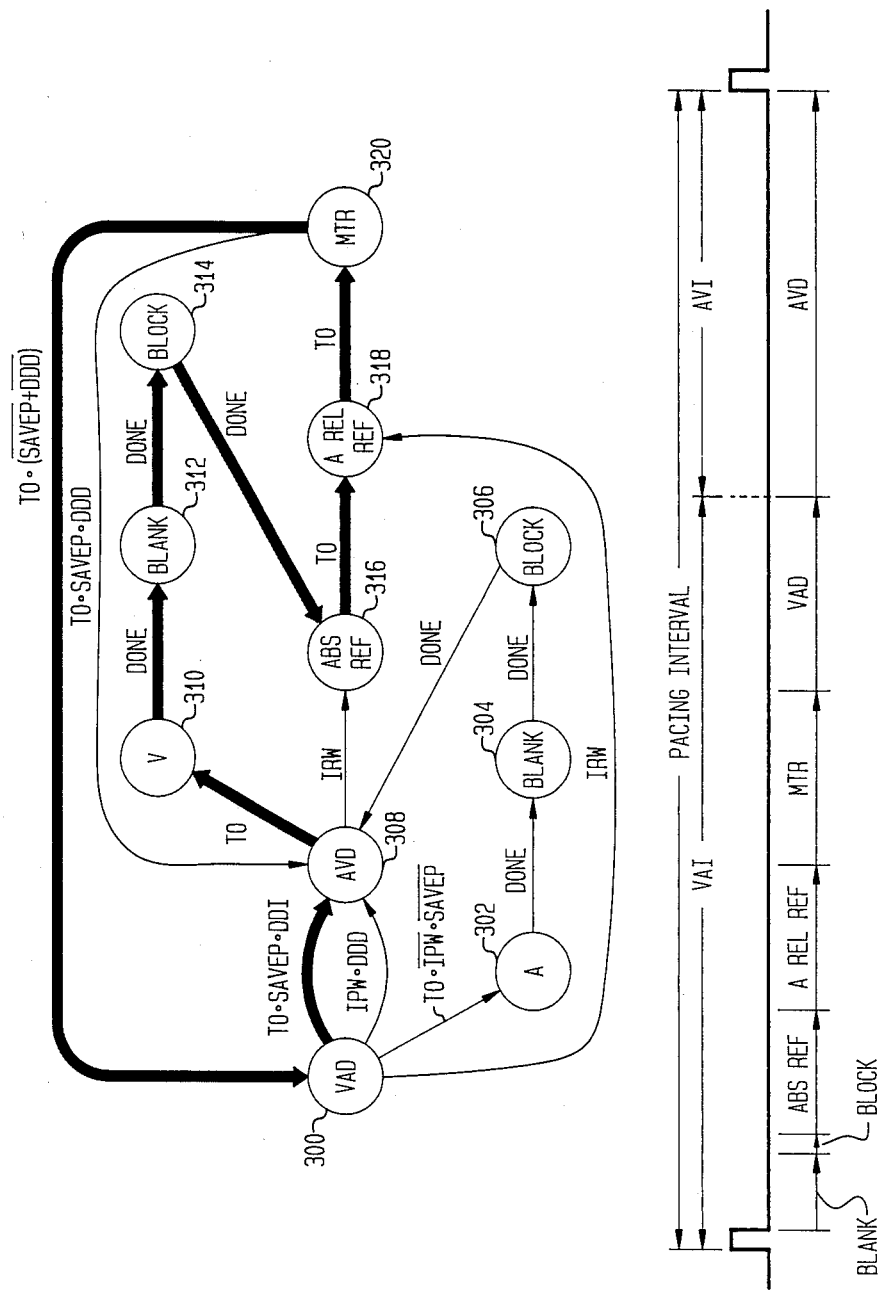
Figure 14C:
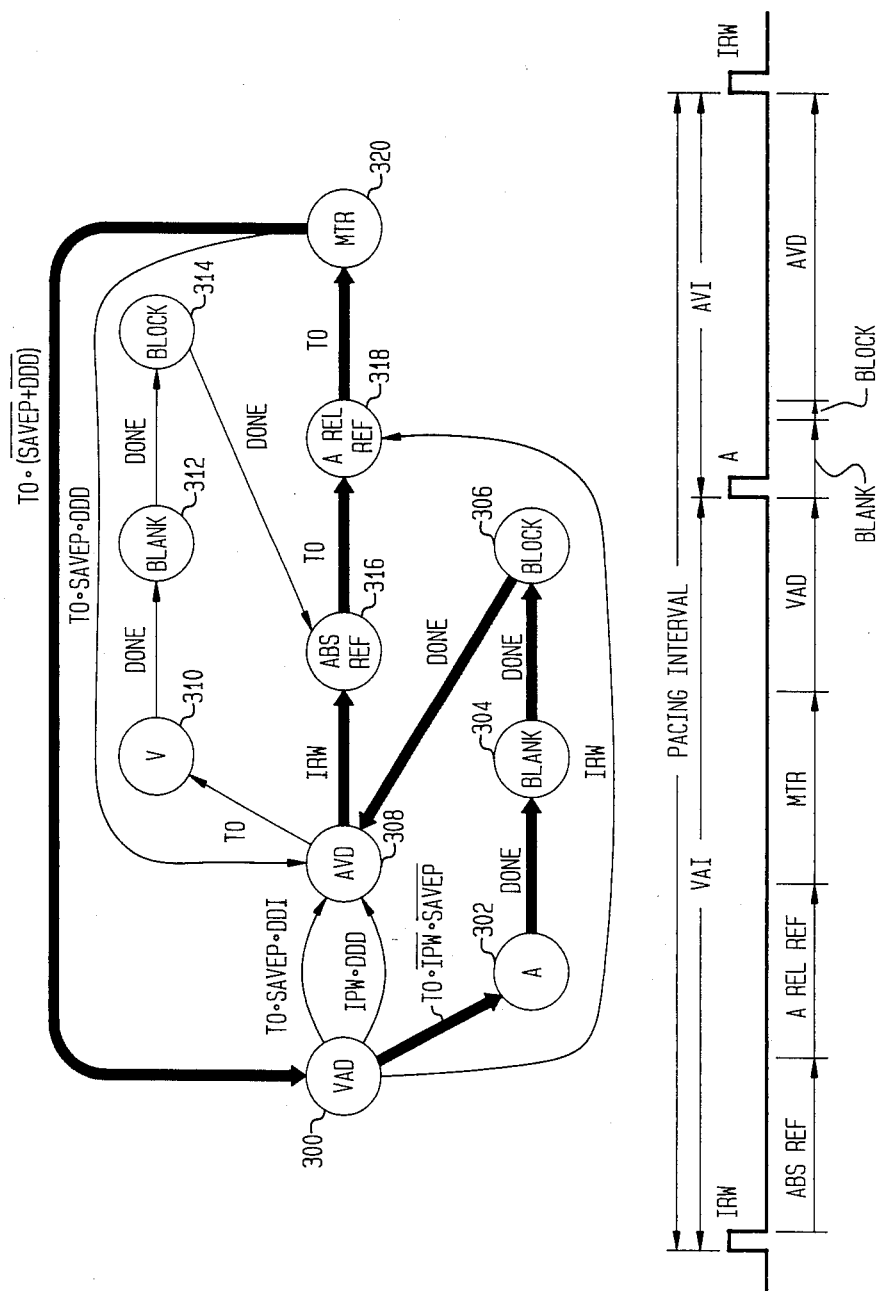

Reference is now made to FIGS. 14A, 14B, and 14C, which figures are state diagrams associated with operation of the preferred embodiment of the pulse generator logic 42 (FIG. 10). What is shown in FIGS. 14A-14C depicts a pacemaker that can operate in either the DDI an DDD modes. As mentioned previously, it is to be understood that the present invention is not limited to a pacemaker that can operate only in DDI or DDD modes. The state diagrams shown in FIGS. 14A-14C are helpful in understanding the various timing sequences that are associated with the pulse generator logic. With the aid of such diagrams, those skilled in the art could readily realize the logic circuitry necessary to build the appropriate control logic. Reference is also made to copending patent application Ser. No. 574,707, assigned to the same assignee as is this application, filed 01/27/84, for a more detailed description of representative circuits that could be employed to realize the pulse generator and other logic circuits of a complex, multimode pacemaker. This referenced application contains helpful background information relative to the operation of a modern programmable pacemaker. However, the detailed disclosure presented in the referenced application is not deemed essential to an understanding and use of the present invention.

With reference to the discussion that follows, the terminology of Table 1 should be noted.

TABLE 1

| Term | Definition of Term |
| --- | --- |
| TO | Time out of state preceeding reference |
| IRW | Inhibiting R wave |
| PW | P-wave |
| PNRE | P-wave noise refractory extension |
| IPW | Inhibiting P wave |
| RW | R-wave |
| RNRE | R-wave noise refractory extension |
| SAVEP | "Saved P" Pulse sensed during relative refractory period |
| API | A-P interval measurement |
| ARI | A-R interval measurement |
| VAD | V-A delay - programmable |
| A | A-pulse |
| V | V-Pulse |
| ABS REF | Absolute refractory - extendable if P-wave sensed |
| MTR | Maximum tracking rate interval - programmed |
| IPW | PW PNRE |
| PW | P DVI AVD ABS REF BLOCK BLANK A V |
| IRW | RE RNRE |
| RW | R ABS REF BLOCK BLANK A V |

Referring now to FIG. 14a, the state diagram associated with operation of the pulse generator logic 42 (FIG. 10) is indicated. Highlighted in FIG. 14a, (in bold lines) is the path that the pulse generator logic would follow assuming that both an A-pulse and a V-pulse are generated. This will now be explained. Beginning with the VAD state 300, which state indicates that the V-A delay (a programmable delay) is in the process of timing out, the sequence is initiated. When VAD has timed out, and in the absence of IPW and SAVEP, an A pulse is generated as indicated at 302. After a blanking period, at 304, of approximately 11 msec, followed by a blocking period, at 306, of approximately 2 msec, an AV delay, or AVD, is initiated at 308. The A-V delay is programmable between approximately 125 to 175 msec. At the conclusion of this delay and in the absence of IRW, a V-pulse is generated at 310. When this is completed, there is a further blanking period, at 112, of 11 msec, followed by a blocking period, at 314 of 2 msec, before an Absolute Refractory Period, at 316, is initiated. When the Absolute Refractory Period has timed out, the A Relative Refractory Period begins, as indicated at 318. Once this period has timed out, an interval that in combination with the preceding intervals defines a Maximum Tracking Rate (which interval defines a minimum tracking interval) is initiated, as indicated at 320. Once this interval has timed out, and in the absence of either SAVEP or DDD, the V-A delay period is again initiated back at 300. Thus, a timing cycle or pacing interval is defined as the pulse generator logic moves through these various states. A timing line indicating these various pacing interval events is also included in FIG. 14A. It is noted that the pacing interval comprises the VA interval and the AV interval, each interval of which may contain fixed time intervals and variable time intervals. The fixed timed intervals are programmable through appropriate telemetry controls, or (as is the case with the present invention) through receipt of new VAD or AVD values from the physiological detector.

FIG. 14B is similar to 14A except that no A-pulse is generated because IPW (inhibit P-wave) is present, indicating that a sinus P-wave has been sensed. FIG. 14B assumes that the DDI mode has been enabled, meaning that even though a sinus P-wave has been sensed, as indicated by the presence of SAVEP, the V-A delay is allowed to time out before the A-V delay begins. Once the A-V delay begins, the states change in the same manner as described in connection with FIG. 14A.

FIG. 14C is also similar to FIGS. 14A and 14B, except that only an A-pulse is generated, not a V-pulse. In this figure, during the A-V delay, at 308, IRW is generated, indicating that a naturally occuring R-wave has been sensed. Hence, there is no need to generate a V-pulse in order to stimulate the ventricle.

It should be evident from FIGS. 14A-14C that only a small number of the various possible types of timing cycles have been illustrated. However, as those skilled in the art will recognize, the state diagrams of these figures include therein a large number of such possible combinations. It should also be emphasized that the state diagrams of FIGS. 14A-14C are only representative of the types of state diagrams that may be employed with programmable pacemakers. It is again emphasized that the present invention is not directly concerned with the type of state diagram that is employed, but rather with a means for adjusting VAD and AVD with the goal of adjusting the pacing interval so that the heart rate can be adjusted as a function of sensed physiological need. As such, it will be apparent that other timing intervals (besides VAD and AVD) included within the cycles shown in FIGS. 14A–14C could be adjusted as a function of the API, ARI, or VRI measurements in order to adjust the pacing interval, and hence, the heart rate.

FIG. 15 depicts some further state diagrams that relate to the state diagrams of FIGS. 14A–14C. Terminology used in connection with the diagrams of FIG. 15 is also found in Table 1. FIG. 15A, for example, illustrates that the SAVEP state is entered by the generation of an IPW signal (which signal is generated whenever a P-wave is sensed). Similarly, this state is disabled at the end of the absolute refractory period, or ABS REF.

FIGS. 15B and 15C illustrate the R-wave noise refractory extension state, RNRE, and the P-wave noise refractory extension state, PNRE. The enabling of these states determines whether the IPW and IRW signals are generated, as indicated in Table 1.

Referring to FIGS. 15D and 15E, two additional states are shown that are used in conjunction with one embodiment of the present invention. The API state is a state wherein the A-P interval measurement is enabled. This state is illustrated in FIG. 15D. Similarly, the ARI state is a state that indicates that the A-R interval measurement is enabled. This is illustrated in FIG. 15E. From FIG. 15D, it is seen that the API state, once enabled, is disabled if a time out occurs or if an IPW signal is generated, which IPW signal indicates that a sinus P-wave has been sensed. A time out period is assigned to the API state in order to account for the possibility that a paced P-wave may not occur in response to an A-pulse, (i.e., P-wave capture does not occur) or in case there is a failure to sense the P-wave for whatever reason. Further, in some patients, there may be several heart cycles where no P-wave occurs.

Appendix B, submitted herewith, provides additional information relative to incorporating the teachings of the present invention into a multi-mode programmable pacemaker.

Given the above description of the present invention, one skilled in the art could readily design and realize the appropriate circuitry for carrying out the invention. It is emphasized that the actual circuit details associated with the pacemaker design are not critical to an understanding or use of the present invention. Rather, any suitable scheme or circuitry that allows A-P, A-R, or V-R measurements to be made, and then processes these measurements in order to adjust the various timing intervals that control the pacing rate, could be employed, and would fall within the scope of the appended claims. As indicted previously, additional background and details associated with the invention may be found in Appendices A and B, filed as a part hereof.

What is claimed is:

1. A cardiac pacemaker for controlling the rate at which a heart beats as a function of physiological need, said heart beat rate defining a cardiac cycle during which atrial and ventricular events occur, said pacemaker comprising:
    means for generating an atrial stimulation pulse (A);
    means for delivering said atrial stimulation pulse to an atrium of the heart in order to trigger atrial depolarization (P);
    means for sensing the occurrence of said triggered atrial depolarization;
    means for measuring the time interval between the generation of said atrial stimulation pulse and said triggered atrial depolarization, said atrial depolarization time interval being referred to as an A-P interval, said A-P interval varying as a function of physiological need; and
    means for adjusting the pacemaker-controlled rate as a function of the measured A-P interval;
    whereby the pacemaker-controlled rate is adjusted as a function of physiological need as sensed by measuring said depolarization time interval.

2. The cardiac pacemaker of claim 1 wherein said means for adjusting the pacemaker-controlled rate as a function of the measured A-P interval includes
    means for counting the number of atrial stimulation pulses generated by said atrial stimulation pulse generation means;
    means for counting the occurrence of cardiac cycles; and
    means for enabling the pacemaker-controlled rate adjustment means only when a prescribed number of atrial stimulation pulses, as counted by said pulse counting means, have been previously generated within a prescribed number of previous consecutive cardiac cycles, as counted by said cardiac cycle counting means.

3. The cardiac pacemaker of claim 1 wherein said triggered atrial depolarization is manifest by the occurrence of a P-wave, and wherein said sensing means includes means for sensing the occurrence of said P-wave, said P-wave having a specified detection point thereon that is used by said sensing means to sense its occurrence.

4. The cardiac pacemaker of claim 3 wherein the detection point of the P-wave comprises the trailing edge of the P-wave, the measured A-P interval therefore including the time from the generation of the atrial stimulation pulse to the trailing edge of the P-wave.

5. The cardiac pacemaker of claim 3 wherein the detection point of the P-wave comprises the peak of the P-wave, the measured A-P interval therefore including the time from the generation of the atrial stimulation pulse to the peak of the P-wave.

6. The cardiac pacemaker of claim 3 wherein the detection point of the P-wave comprises the leading edge of the P-wave, the measured A-P interval therefore including the time from the generation of the atrial stimulation pulse to the leading edge of the P-wave.

7. A cardiac pacemaker having means for generating a stimulation pulse, means for generating a pacing interval, means for controllably delivering said stimulation pulse to a heart at the conclusion of said pacing interval, and means for sensing the physiological need of the heart to be paced at a faster or slower rate, said physiological sensing means comprising:
    sensing means for sensing the occurrence of a cardiac depolarization event, referred to as X, which depolarization event follows the delivery of an atrial stimulation pulse, referred to as A, to the atrium of said heart;
    timing means for measuring the A-X time interval between the delivery of the stimulation pulse A to the atrium of the heart and the occurrence of the sensed cardiac depolarization event X, said A-X time interval thereby comprising the time it takes the heart to depolarize as measured from the time the stimulation pulse is delivered to the heart, said A-X time interval further representing a measured parameter that varies as a function of the physiological need of the heart to beat at a faster or slower rate; and means for controllably adjusting the pacing interval of the pacemaker as a function of the A-X time interval measured by said timing means, whereby stimulation pulses are controllably delivered to the heart at a rate that corresponds to the physiological need of the heart to beat at a faster or slower rate.

8. The cardiac pacemaker of claim 7 wherein said means for controllably adjusting the pacing interval of the pacemaker comprises:
trend identifying means for identifying a trend in the lengthening or shortening of said measured A-X time intervals;
selection means responsive to the identification of the trend identified by said trend identifying means for generating a reference A-X interval; and
conversion means for converting said reference A-X time interval to at least one control parameter for adjusting the value of the pacing interval of the pacemaker.

9. The cardiac pacemaker of claim 7 wherein the cardiac event X sensed by said sensing means comprises the depolarization of the atrium of the heart.

10. The cardiac pacemaker of claim 7 wherein the cardiac depolarization event X sensed by said sensing means comprises the occurrence of a P-wave, the time interval measured by said timing means thus comprising the interval between the generation of the atrial stimulation pulse and the sensing of the P-wave, which time interval is defined as an A-P interval.

11. The cardiac pacemaker of claim 10 wherein said means for controllably adjusting the pacing interval includes response means for sensing and responding to a lengthening of the measured A-P interval by decreasing the pacing interval, thereby increasing the rate at which stimulating pulses are controllably delivered to the heart.

12. The cardiac pacemaker of claim 10 wherein said means for controllably adjusting the pacing interval includes response means for sensing and responding to a lengthening of the measured A-P interval by increasing the pacing interval, thereby decreasing the rate at which stimulating pulses are controllably delivered to the heart.

13. The cardiac pacemaker of claim 7 wherein the cardiac depolarization event X sensed by said sensing means comprises the depolarization, or contraction, of the ventricle of the heart.

14. The cardiac pacemaker of claim 7 wherein the cardiac depolarization event X sensed by said sensing means comprises the occurrence of an R-wave, the time interval measured by said timing means thus comprising the interval between the generation of the atrial stimulation pulse and the sensing of the R-wave, which time interval is defined as an A-R interval.

15. A physiologically-controlled, rate-responsive, demand pacemaker having a pulse generator for selectively generating pacing pulses for delivery to a heart; distribution means for selectively controlling the delivery of the pacing pulses to the heart; and physiological rate adjustment means for adjusting the rate at which the pacing pulses are delivered to the heart as a function of physiological need, said physiological rate adjusting means comprising:
timing means for measuring the depolarization time interval between the generation of a given pacing pulse and the subsequent depolarization or contraction of said heart, said depolarization time interval being a parameter that changes as a function of physiological need; and
means for automatically adjusting the rate at which the pacing pulses are delivered to the heart by said physiological rate adjustment means as a function of the measured depolarization time interval.

16. The pacemaker of claim 15 wherein said automatic pacing pulse rate adjusting means comprises:
cardiac cycle sensing means for sensing the occurrence of a prescribed number of cardiac cycles;
processing means responsive to said cardiac cycle sensing means for generating a reference time interval value derived from the measured time intervals from said prescribed number of prior cardiac cycles; and
rate changing means for changing the rate at which the pacing pulses are delivered to the heart as a function of said reference time interval value.

17. The pacemaker of claim 16 wherein said processing means comprises means for averaging the measured time intervals derived from said prescribed number of cardiac cycles, said reference time interval value thereby comprising an average time interval of the time intervals measured during said prescribed number of cardiac cycles, said rate changing means including means for changing the pacing pulse delivery rate as a function of said average time interval.

18. The pacemaker of claim 16 wherein said processing means includes trend-identification means for identifying trend changes in the time intervals measured during said prescribed number of cardiac cycles, said rate changing means including means for changing the rate at which pacing pulses are delivered to the heart only when there is an identified trend change in said measured time intervals.

19. The pacemaker of claim 18 wherein said trend identification means includes means for determining whether said timing means has successfully measured said time interval for three consecutive cardiac cycles and all three of the corresponding time interval measurements are greater than or less than the reference time interval value from a prior processed group of time interval measurements.

20. The pacemaker of claim 15 wherein the depolarization time interval measured by said timing means comprises the time interval between the delivery of an atrial pacing pulse and the subsequent depolarization of the atrium.

21. The pacemaker of claim 15 wherein the depolarization time interval measured by said timing means comprises the time interval between the delivery of an atrial pacing pulse and the subsequent depolarization of the ventricle.

22. A pacemaker having sensing and stimulating means coupled to the ventricle of a heart, said pacemaker comprising
means for generating a ventricular stimulation pulse and delivering said pulse to the ventricle through said stimulating means;
means for measuring the depolarization time of the ventricle, said depolarization time comprising a V-R time interval that equals the time between the delivery of said ventricular stimulation pulse to the ventricle and the sensing, by said sensing means, of an R-wave;
means for generating a control signal as a function of said measured V-R time interval; and means for adjusting a pacing rate of said pacemaker as a function of said control signal, said pacing rate controlling the rate a which said heart beats.

23. The pacemaker of claim 22 wherein said means for measuring the V-R time interval includes processing means for processing the measured V-R time interval over a plurality of previous cardiac cycles and for generating a reference V-R measurement as a result of said processing, said control signal generating means including means responsive to said reference V-R measurement for adjusting the value of said control signal.

24. The pacemaker of claim 23 wherein said processing means includes smoothing means for controlling the rate at which said reference V-R measurement is allowed to change.

25. The pacemaker of claim 23 wherein said processing means includes means for averaging the measured V-R time intervals and for generating an average V-R time interval value as a result of said averaging and for affecting the value of said reference V-R measurement as a function of said average V-R time interval value.

26. The pacemaker of claim 23 wherein said processing means includes trend-identification means for identifying trend changes in the measured V-R time intervals and for generating an acceptable trend signal, said acceptable trend signal indicating that the V-R time intervals are changing in the same direction, said pacing rate adjustment means including means responsive to said acceptable trend signal for adjusting said pacing rate.

27. The pacemaker of claim 26 wherein said trend-identification means includes means for generating said acceptable trend signal when the measured V-R intervals from at least the previous three consecutive cardiac cycles are all greater than or less than a most recently generated reference V-R measurement.

28. A method for physiologically adjusting the pacing interval of a pacemaker, said pacemaker including means for generating an atrial pacing pulse, means for delivering the atrial pacing pulse to the atrium of a heart, and means for sensing the depolarization of the atrium in response to the delivered atrial pacing pulse, said method comprising the steps of:
   (a) generating an atrial pacing pulse and delivering said atrial pacing pulse to the atrium of the heart;
   (b) sensing the depolarization of the atrium resulting from the delivered atrial pacing pulse;
   (c) measuring the time interval between the generation of the atrial pacing pulse and the occurrence of the atrial depolarization, said time interval comprising an atrial depolarization time interval; and
   (d) using the atrial depolarization time interval as a control parameter to adjust the pacing interval of the pacemaker.

29. The method of claim 28 wherein step (d) comprises processing the depolarization time intervals measured in step (c) over a plurality of prior cardiac cycles, and generating a reference depolarization time interval that is representative of a trend in the lengthening or shortening of the processed depolarization time interval measurements.

30. A method for physiologically adjusting the pacing interval of a pacemaker, said pacemaker including means for generating a ventricular pacing pulse, means for delivering the ventricular pacing pulse to the ventricle of a heart, and means for sensing the depolarization of the ventricle in response to the delivered ventricular pacing pulse, said method comprising the steps of:
   (a) generating a ventricular pacing pulse and delivering said ventricular pacing pulse to the ventricle of the heart;
   (b) sensing the depolarization of the ventricle resulting from the delivered ventricular pacing pulse;
   (c) measuring the time interval between the generation of the ventricular pacing pulse and the occurrence of the ventricular depolarization, said time interval comprising a ventricular depolarization time interval; and
   (d) using the ventricular depolarization time interval as a control parameter to adjust the pacing interval of the pacemaker.

31. The method of claim 30 wherein step (d) comprises processing the depolarization time intervals measured in step (c) over a plurality of prior cardiac cycles, and generating a reference depolarization time interval that is representative of a trend in the lengthening or shortening of the processed depolarization time interval measurements.

32. A method for physiologically adjusting the pacing interval of a pacemaker, said pacemaker including means for generating an atrial pacing pulse, means for delivering the atrial pacing pulse so the atrium of the heart, means for sensing the depolarization of the atrium in response to the delivered atrial pacing pulse, and means for sensing the depolarization of the ventricle following the atrial depolarization, said method comprising the steps of:
   (a) generating an atrial pacing pulse and delivering said atrial pacing pulse to the atrium of the heart;
   (b) sensing the depolarization of the atrium resulting from the delivered atrial pacing pulse;
   (c) sensing the depolarization of the ventricle following the atrial depolarization sensed in step (b);
   (d) measuring the time interval between the generation of the atrial pacing pulse and the atrial depolarization sensed in step (b);
   (e) measuring the time interval between the generation of the atrial pacing pulse and the ventricular depolarization sensed in step (c); and
   (f) adjusting the pacing interval of the pacemaker as a function of a specified one of the time intervals measured in step (d) or (e).

33. The method of claim 32 wherein the specified time interval comprises the atrial-pacing-pulse-to-atrial-depolarization time interval measured in step (d).

34. The method of claim 32 wherein the specified time interval comprises the atrial-pacing-pulse-to-ventricular-depolarization time interval measured in step (e).

35. The method of claim 32 wherein step (f) comprises processing the specified time intervals measured in steps (d) or (e) over a plurality of prior cardiac cycles, and generating a reference time interval from said processing that is representative of a trend in the lengthening or shortening of these time interval measurements, said reference time interval being used as said control parameter to adjust the pacing interval of the pacemaker.

36. A method for physiologically adjusting the pacing interval of a pacemaker, said pacemaker including means for generating an atrial pacing pulse, means for delivering the atrial pacing pulse to the atrium of the heart, means for sensing the depolarization of the atrium in response to the delivered atrial pacing pulse, means for generating a ventricular pacing pulse, means for delivering the ventricular pacing pulse to the ventricle of the heart, and means for sensing the depolarization of the ventricle, said method comprising the steps of:

(a) generating one of said atrial or ventricular pacing pulses and delivering said pacing pulse to the appropriate chamber of the heart;
(b) sensing the depolarization of the heart chamber to which the pacing pulse is delivered;
(c) measuring the time interval between the generation of the specified pacing pulse and a specified sensed depolarization, said time interval comprising a depolarization time interval; and
(d) adjusting the pacing interval of the pacemaker as a function of the time interval measured in step (c).

37. The method of claim 36 wherein the specified pacing pulse comprises the ventricular pacing pulse and the specified depolarization comprises the ventricular depolarization that occurs in response to the delivery of the ventricular pacing pulse.

38. The method of claim 36 wherein the specified pacing pulse comprises the atrial pacing pulse and the specified depolarization comprises the atrial depolarization that occurs in response to the delivery of the atrial pacing pulse.

39. The method of claim 36 wherein the specified pacing pulse comprises the atrial pacing pulse and the specified depolarization comprises the ventricular depolarization that follows the atrial depolarization occurring in response to the delivery of the atrial pacing pulse.

40. A method for measuring the atrial depolarization time of a heart, said atrial depolarization time being referred to as an A-P interval, said heart being stimulated by an atrial stimulation pulse delivered to the atrium of the heart from a pacemaker through an atrial lead, said atrial lead having first and second spaced-apart electrodes in contact with the atrium, said atrial lead providing electrical contact between an atrial stimulation pulse generator within said pacemaker and said first electrode, and said atrial lead further providing electrical contact between a P-wave sensing amplifier within said pacemaker and said second electrode, said measured A-P interval being usable by said pacemaker as a parameter indicative of physiological need, said method comprising the steps of:

(a) stimulating the atrium with pulses generated by said atrial stimulation pulse generator;
(b) monitoring the output of said P-wave sensing amplifier to detect the occurrence of a P-wave in response to the pulse provided in step (a); and
(c) measuring the time interval between the occurrence of one of said pulses generated by said atrial stimulation pulse generator and the detection of a P-wave as sensed at the output of said P-wave sensing amplifier in step (b);

the time interval measured in step (c) providing a measure of the atrial depolarization time, said atrial depolarization time providing, in turn, a relative measure of physiological need at the time the measurement is made.

41. The method of claim 40 further including the step of:

(d) processing the time interval measured in step (c) over a plurality of consecutive occurrences thereof in order to produce a reference time interval measurement that represents all of the time interval measurements from said previous plurality of consecutive occurrences, said reference time interval measurement comprising a measure of the atrial depolarization time over time, said reference time interval measurement thereby providing a measure of physiological need over time.

42. The method of claim 40 further including the steps of:

(d) processing the time interval measured in step (c) over a plurality of consecutive occurrences thereof in order to determine if said time interval measurements are changing in the same direction;
(e) generating a trend signal in response to a finding in step (d) that the time interval measurements are changing in the same direction, said trend signal providing an indication that physiological need is changing in the same direction, whereby an indication is provided as to whether the heart needs to beat faster or slower.

43. The method of claim 42 further including the step of:

(f) generating a reference time interval that reflects the unidirectional changes in said time interval measurements as determined in step (d), said reference time interval providing an indication of the amount of change in physiological need.

44. A method for measuring the ventricular depolarization time of a heart, said ventricular depolarization time being referred to as a V-R interval, said heart being stimulated by a ventricular stimulation pulse delivered to the ventricle of the heart from a pacemaker through a ventricular lead, said ventricular lead having first and second spaced-apart electrodes in contact with the ventricle, said ventricular lead providing electrical contact between a ventricular stimulation pulse generator within said pacemaker and said first electrode, and said ventricular lead further providing electrical contact between an R-wave sensing amplifier within said pacemaker and said second electrode, said measured V-R interval being usable by said pacemaker as a parameter indicative of physiological need, said method comprising the steps of:

(a) stimulating the ventricle with pulses generated by said ventricular stimulation pulse generator;
(b) monitoring the output of said R-wave sensing amplifier to detect the occurrence of an R-wave in response to the pulse provided in step (a); and
(c) measuring the time interval between the occurrence of one of said pulses generated by said ventricular stimulation pulse generator and the detection of an R-wave as sensed at the output of said R-wave sensing amplifier in step (b); the time interval measured in step (c) providing a measure of the ventricular depolarization time, said ventricular depolarization time providing, in turn, a relative measure of physiological need at the time the measurement is made.

45. The method of claim 44 further including the step of:

(d) processing the time interval measured in step (c) over a plurality of consecutive occurrences thereof in order to produce a reference time interval measurement that represents all of the time interval measurements from said previous plurality of consecutive occurrences, said reference time interval measurement comprising a measure of the ventricular depolarization time over time, said reference time interval measurement thereby providing a measure of physiological need over time.

46. The method of claim 44 further including the steps of:

(d) processing the time interval measured in step (c) over a plurality of consecutive occurrences thereof in order to determine if said time interval measurements are changing in the same direction;

(e) generating a trend signal in response to a finding in step (d) that the time interval measurements are changing in the same direction, said trend signal providing an indication that physiologial need is changing in the same direction, whereby an indication is provided as to whether the heart needs to beat faster or slower.

47. The method of claim 46 further including the step of:

(f) generating a reference time interval that reflects the unidirectional changes in said time interval measurements as determined in step (d), said reference time interval providing an indication of the amount of change in physiological need.

* * * * *